(12) United States Patent
Pingali et al.

(10) Patent No.: US 8,268,867 B2
(45) Date of Patent: Sep. 18, 2012

(54) 1,3-DIOXANE CARBOXYLIC ACIDS

(75) Inventors: Harikishore Pingali, Gujarat (IN); Pankaj Maganlal Makadia, Gujarat (IN); Braj Bhushan Lohray, Gujarat (IN); Vidya Bhushan Lohray, Gujarat (IN); Pankaj Ramanbhai Patel, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 388 days.

(21) Appl. No.: 12/279,407

(22) PCT Filed: Feb. 19, 2007

(86) PCT No.: PCT/IN2007/000066
§ 371 (c)(1),
(2), (4) Date: Aug. 27, 2010

(87) PCT Pub. No.: WO2007/099553
PCT Pub. Date: Sep. 7, 2007

(65) Prior Publication Data
US 2010/0311795 A1 Dec. 9, 2010

(30) Foreign Application Priority Data
Feb. 27, 2006 (IN) .......................... 270/MUM/2006

(51) Int. Cl.
*A61K 31/4433* (2006.01)
*C07D 405/12* (2006.01)
(52) U.S. Cl. ..................................... 514/336; 546/282.4
(58) Field of Classification Search .................. 514/336; 546/282.4
See application file for complete search history.

(56) References Cited

FOREIGN PATENT DOCUMENTS
WO    2005/077943    8/2005

*Primary Examiner* — Taofiq A Solola
(74) *Attorney, Agent, or Firm* — Ladas & Parry LLP

(57) ABSTRACT

The present invention relates to novel 1,3-dioxane carboxylic acids of the general formula (I), their tautomeric forms, their stereoisomers, their pharmaceutically acceptable salts, pharmaceutical compositions containing them, methods for their preparation, use of these compounds in medicine and the intermediates involved in their preparation.

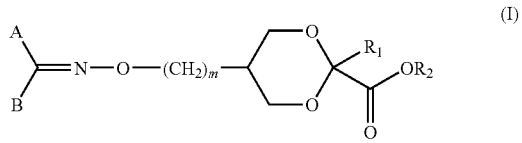

(I)

20 Claims, No Drawings

1,3-DIOXANE CARBOXYLIC ACIDS

FIELD OF INVENTION

The present invention relates to novel 1,3-dioxane carboxylic acids of the general formula (I), their tautomeric forms, their stereoisomers, their pharmaceutically acceptable salts, pharmaceutical compositions containing them, methods for their preparation, use of these compounds in medicine and the intermediates involved in their preparation.

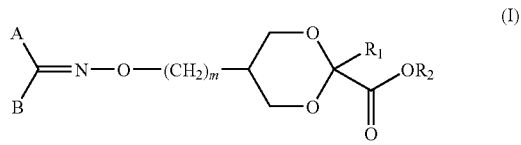

The compounds of the general formula (I) lower blood glucose, lower or modulate triglyceride levels and/or cholesterol levels and/or low-density lipoproteins (LDL) and raises the high-density lipoproteins (HDL) plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

The compounds of the present invention can be useful as aldose reductase inhibitors; for improving cognitive functions in dementia, and in the treatment and/or prophylaxis of disorders such as psoriasis, polycystic ovarian syndrome (PCOS), cancer, osteoporosis, leptin resistance, inflammation and inflammatory bowel diseases, xanthoma, pancreatitis, myotonic dystrophy, endothelial cell dysfunction and hyperlipidemia.

BACKGROUND OF THE INVENTION

Hyperlipidemia has been recognized as the major risk factor in causing cardiovascular diseases due to atherosclerosis. Atherosclerosis and other such peripheral vascular diseases affect the quality of life of a large population in the world. The therapy aims to lower the elevated plasma LDL cholesterol, low-density lipoprotein and plasma triglycerides in order to prevent or reduce the risk of occurrence of cardiovascular diseases. The detailed etiology of atherosclerosis and coronary artery diseases is discussed by Ross and Glomset [*New Engl. J. Med,* 295, 369-377 (1976)]. Plasma cholesterol is generally found esterified with various serum lipoproteins and numerous studies have suggested an inverse relationship between serum HDL-cholesterol level and risk for occurrence of cardiovascular disease. Many studies have suggested an increased risk of coronary artery diseases (CAD) due to elevated LDL and VLDL-cholesterol levels [Stampfer et al., *N. Engl. J. Med.,* 325, 373-381 (1991)]. The other studies illustrate protective effects of HDL against progression of atherosclerosis. Thus, HDL has become a crucial factor in treating diseases with increased levels of cholesterol [Miller et. al., *Br. Med.* 1282, 1741-1744 (1981); Picardo et al., *Arteriosclerosis,* 6, 434-441 (1986); Macikinnon et al., *J. Biol. Chem.* 261, 2548-2552 (1986)].

Diabetes is associated with a number of complications and also affect a large population. This disease is usually associated with other diseases such as obesity, hyperlipidemia, hypertension and angina. It is well established that improper treatment can aggravate impaired glucose tolerance and insulin resistance, thereby leading to frank diabetes. Further, patients with insulin resistance and type 2 diabetes often have raised triglycerides and low HDL-cholesterol concentrations and therefore, have greater risk of cardiovascular diseases. The present therapy for these diseases includes sulfonylureas and biguanides along with insulin. This type of drug therapy may lead to mild to severe hypoglycemia, which may lead to coma or in some cases may lead to death, as a result of unsatisfactory glycemic control by these drugs. Recent addition of drugs in the treatment of diabetes are the thiazolidinediones, drugs having insulin-sensitizing action. Thiazolidinediones like troglitazone, rosiglitazone and pioglitazone are prescribed alone or in combination with other anti-diabetic agents.

These are useful in treating diabetes, lipid metabolism but are suspected to have tumor-inducing potential and cause hepatic dysfunction, which may lead to liver failure. Further, serious undesirable side-effects have occurred in animal and/or human studies which include cardiac hypertrophy, haemodilution and liver toxicity in a few glitazones progressing to advanced human trials. The drawback is considered to be idiosyncratic. Presently, there is a need for a safe and an effective drug, to treat insulin resistance, diabetes and hyperlipidemia. [*Exp. Clin. Endocrinol. Diabetes:* 109(4), S548-9 (2001)]

Obesity is another major health problem being associated with increased morbidity and mortality. It is a metabolic disorder, in which excess of fat is accumulated in the body. Although, its etiology is unclear, the general feature includes excess of calorie intake than it is consumed. Various therapies such as dieting, exercise, appetite suppression, inhibition of fat absorption etc. have been used to combat obesity. However, more efficient therapies to treat this abnormality is essential as obesity is closely related to several diseases such as coronary heart disease, stroke, diabetes, gout, osteoarthritis, hyperlipidemia and reduced fertility. It also leads to social and psychological problems [*Nature Reviews: Drug Discovery:* 1(4), 276-86 (2002)].

Peroxisome Proliferator Activated Receptor (PPAR) is a member of the steroid/retinoid/thyroid hormone receptor family. PPAR∝, PPARγ and PPARδ have been identified as subtypes of PPARs. Extensive reviews regarding PPARs, their role in different diseased conditions are widely published [*Endocrine Reviews,* 20(5), 649-688 (1999); *J. Medicinal Chemistry,* 43(4), 58-550 (2000); *Cell,* 55, 932-943 (1999); *Nature,* 405, 421-424 (2000); *Trends in Pharmacological Sci.,* 469-473 (2000)]. PPARγ activation has been found to play a central role in initiating and regulating adipocyte differentiation [*Endocrinology* 135, 798-800, (1994)] and energy homeostasis, [*Cell,* 83, 803-812 (1995); Cell, 99, 239-242 (1999)]. PPARγ agonists would stimulate the terminal differentiation of adipocyte precursors and cause morphological and molecular changes characteristic of a more differentiated, less malignant state. During adipocyte differentiation, several highly specialized proteins are induced, which are being involved in lipid storage and metabolism. It is accepted that PPARγ activation leads to expression of CAP gene [*Cell Biology,* 95, 14751-14756, (1998)], however, the exact link from PPARγ activation to changes in glucose metabolism and decrease in insulin resistance in muscle has not been clear. PPARα is involved in stimulating β-oxidation of fatty acids [*Trends Endocrine. Metabolism,* 4, 291-296 (1993)] resulting in plasma circulating free fatty acid reduction [*Current Biol.,* 5, 618-621 (1995)]. Recently, role of PPARγ activation in the terminal differentiation of adipocyte precursors has been implicated in the treatment of cancer. [*Cell,* 79, 1147-1156 (1994); *Cell,* 377-389 (1996); *Molecular Cell,* 465-470 (1998); Carcinogenesis, 1949-1953 (1998); *Proc. Natl. Acad. Sci.,* 94, 237-241 (1997); *Cancer Research,* 58, 3344-3352 (1998)]. Since PPARγ is expressed in certain cells consistently, PPARγ agonists would lead to nontoxic chemotherapy. There is growing evidence that PPAR agonists may also influence the cardiovascular system through PPAR receptors as well as directly by modulating vessel wall function [*Med. Res. Rev.,* 20 (5), 350-366 (2000)].

PPAR α agonists have been found useful in the treatment of obesity (WO 97/36579). Dual PPAR α and γ agonists have been suggested to be useful for Syndrome X (WO 97/25042). PPAR γ agonists and HMG-CoA reductase inhibitors have exhibited synergism and indicated the usefulness of the combination in the treatment of atherosclerosis and xanthoma (EP 0753298).

Leptin is a protein when bound to leptin receptors is involved in sending satiety signal to the hypothalamus. Leptin resistance would therefore lead to excess food in-take, reduced energy expenditure, obesity, impaired glucose tolerance and diabetes [*Science,* 269, 543-46 (1995)]. It has been reported that insulin sensitizers lower plasma leptin concentration [*Proc. Natl. Acad. Sci.* 93, 5793-5796 (1996): WO 98/02159].

Several compounds have been reported which are dual agonists of PPAR α and γ like alkoxy phenyl propanoic acid derivatives, aryloxy propanoic acid derivatives, benzyl glycine derivatives etc have been reported and are in various developmental stages.

US 20030166697 (Nippon Shinayaku) discloses compounds of the following general formula:

R₁-Het-D-E wherein

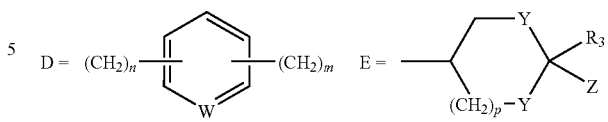

$R_1$ represents (un)substituted aryl, aromatic heterocyclic or cycloalkyl groups; 'Het' is an optionally substituted divalent aromatic heterocyclic group; W is —CH— or N; m=1-10; n=0-9; p=0-2; Y=O or S; $R_3$ is H or alkyl; Z=carboxy, alkoxy carbonyl etc. WO 2000004011 discloses compounds having the following general formula for the treatment of dyslipidemia, atherosclerosis and diabetes;

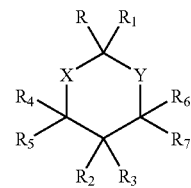

where X, Y=CH₂, O, S, NR$_a$ (R$_a$=H, alkyl, aryl, etc.); R=H, alkyl, cycloalkyl, etc.; R¹=H, alkyl, hydroxyalkyl, —(CH₂)$_t$—COOR$_c$ where t=0-6 & R$_c$ represents H or alkyl group, etc.; R₂ & R₃=H, alkyl, cycloallyl, (C₆-C₁₀)aryl, (C₆-C₁₀)aryl(C₁-C₇)alkyl, 3-10 membered optionally substituted heterocyclic group etc.; or R₂ & R₃ optionally form a chain —(CH₂)$_{r1}$ (r1 =2-5), etc.; R₄-R₇=H, alkyl, (un)substituted aryl, etc.

However, the therapeutic potential of these compounds to treat diseases has not yet been proved and so there remains the need to develop newer medicines which are better or of comparable efficacy with the present treatment regimes, have lesser side effects and require a lower dosage regime We herein disclose novel compounds of formula (I) useful as hypocholesterolemic, hypolipidemic, hypolipoproteinemic, anti-obesity and antihyperglycemic agents which may have additional body weight lowering effect and beneficial effect in the treatment and/or prophylaxis of diseases caused by hyperlipidemia, diseases classified under Syndrome X and atherosclerosis, and methods for their preparation.

Preferred Embodiments of the Invention

The main objective of the present invention is to provide novel substituted 1,3 dioxane carboxylic acids and their derivatives represented by the general formula (I), their tautomeric forms, their stereoisomers, their pharmaceutically acceptable salts, and pharmaceutical compositions containing them or their mixtures thereof.

In an embodiment of the present invention is provided a process for the preparation of novel substituted 1,3 dioxane carboxylic acids and their derivatives represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

DETAILED DESCRIPTION OF THE INVENTION

Accordingly, the present invention relates to compounds of the general formula

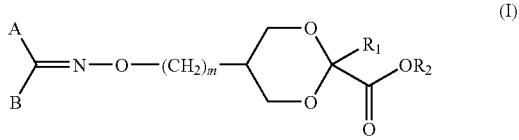

their tautomeric forms, their stereoisomers, their pharmaceutically acceptable salts, and pharmaceutical compositions containing them wherein
'A' represents an optionally substituted single or fused group selected from ary, heteroaryl, heterocyclyl groups;
'B' represents substituted or unsubstituted linear or branched ($C_1$-$C_6$)alkyl group;
'm' represent an integer from 2-6;
$R_1$ represents ($C_1$-$C_3$)alkyl group
$R_2$ represents hydrogen, linear or branched ($C_1$-$C_3$) alkyl group.

The aryl group may be an aromatic system containing one, two or three rings wherein such rings may be attached together in a pendant manner or may be fused; in a preferred embodiment such aryl group may be selected from phenyl, naphthyl, tetrahydronaphthyl, indane, biphenyl groups;

The heteroaryl group represents 5 to 8 membered aromatic radicals, which may be single or fused containing one or more hetero atoms selected from O, N or S; in a preferred embodiment such groups may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzothiazolyl, benzimidazolyl, benzotriazolyl, phthalazynil, naphthylidinyl, purinyl, carbazolyl, phenothiazinyl, phenoxazinyl groups;

The term "heterocyclyl" represents saturated, partially saturated and unsaturated ring-shaped radicals, the heteroatoms selected from nitrogen, sulfur and oxygen; in a preferred embodiment such groups may be selected from pyrrolidinyl, imidazolidinyl, piperidinyl, piperazinyl, morpholinyl, oxazolidinyl, thiazolidinyl, and the like; examples of partially saturated heterocyclic radicals, include clihydrothiophene, dihydropyran, dihydrofuran, dihydrothiazole groups;

When A is substituted, the substituents may be selected from hydroxyl, oxo, halo, thio, amino, or substituted or unsubstituted groups selected from alkyl, haloalkyl, aminoalkyl, alkoxy, alkoxyalkyl, haioalkoxy, cycloalkyl, alkoxy, cycloalkoxy, aryl, aryloxy, aralkyl, aralkoxy, heteroaryl, heteroaralkyl, heteroaryloxy, acyl, acyloxy, hydroxyallyl, alkoxyalkyl, aryloxyalkyl, aralkoxyalkyl, alkylthio, thioalkyl, aminocarbonyl, arylthio, alkylsulfonyloxy, sulfenyl derivatives, sulfonyl derivatives.

When the substituents on 'A' are further substituted, those substituents are selected from hydroxyl, oxo, halo, thio, or substituted or unsubstituted groups selected from alkyl, haloalkyl, alkoxy, haloalkoxy, acyl, acyloxy, alkylthio, thioalkyl, alkylsulfouyloxy, ulkoxycarbonylamino, sulfenyl derivatives, sulfonyl derivatives.

The various groups, radicals and substituents used anywhere in the specification are described in the following paragraphs.

In a further preferred embodiment the groups, radicals described above may be selected from:
the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, n-heptyl, iso-heptyl, n-octyl, iso-octyl and the like;
the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together;
the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;
the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;
the "haloalkoxy" group is selected from suitable haloalkyl, as defined above, directly attached to an oxygen atom, more preferably groups selected from fluoromethoxy, chloromethoxy, fluoroethoxy, chloroethoxy and the like;
the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;
the "heterocyclic" or "heterocyclic" group used either alone or in combination with other radicals, is selected from suitable saturated, partially saturated or unsaturated aromatic or non aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, a zaquinazolinoyl, thienopyrimidonyl, quinazolonyl, pyrimidonyl, benzoxazinyl, benzoxazinonyl, benzothiazinyl, benzothiazinonyl, thieno piperidinyl, and the like;
the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the groups "heteroaryloxy", "heteroaralkoxy", "heterocycloxy", "heterocylylalkoxy" are selected from suitable heteroaryl, heteroarylallyl, heterocyclyl, heterocylylalkyl groups respectively, as defined above, attached to an oxygen atom;

the term "aralkyl" refers to an aryl group as defined above, directly attached to an alkyl group as defined above, at one or more positions;

the term "aralkoxy" refers to an aralkyl group, as defined above attached directly to an oxygen atom;

the terms "cycloalkoxy" and "aryloxy" refers to a cycloalkyl group and an aryl group respectively, as defined above, attached directly to an oxygen atom;

the term "heteroaralky" used herein, either alone or in combination with other radicals, denotes a heteroaryl group, as defined above, attached to a straight or branched saturated carbon chain containing 1 to 6 carbons, such as (2-furyl)methyl, (3-furyl)methyl, (2-thienyl)methyl, (3-thienyl)methyl, (2-pyridyl)methyl, 1-methyl-1-(2-pyrimidyl)ethyl and the like;

the term "aryloxyalkyl" used herein, alone or in combination with other radicals, includes phenoxymethyl, napthyloxymethyl, and the like; the term "aralkoxyalkyl" used herein, alone or in combination with other radicals, includes $C_6H_5CH_2OCH_2$, $C_6H_5CH_2OCH_2CH_2$, and the like;

the term "arylthio" used herein, either alone or in combination with other radicals, refers to an aryl group, as defined above, linked through a divalent sulfur atom, having a free valence bond from the sulfur atom such as phenylthio, napthylthio and the like;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, to benzoyl and the like, which may be substituted;

the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "aminocarbonyl" group used either alone or in combination with other radicals, may be selected from 'aminocarbonyl', 'aminocarbonylalkyl', "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote aminocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "allylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic allylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or $R_x$SO, where $R_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like;

the "alkylsulfonyloxy" group used either alone or in combination, refers to an alkylsulfonyl group as defined above, attached directly to an oxygen atom.

Suitable groups and substituents on the groups may be selected from those described anywhere in the specification. Particularly useful compounds may be selected from Methyl-2-methyl-5-[4-(1-phenyl-ethylideneaminooxy)-butyl]-[1,3]dioxane-2-carboxylate;

Methyl-2-methyl-5-[4-(1-phenyl-pentylideneaminooxy)-butyl]-[1,3]dioxane-2-carboxylate;

Methyl-5-(4-benzylideneaminooxy-butyl)-2-methyl-[1,3]dioxane-2-carboxylate;

Methyl-2-methyl-5-{4-[1-(4-trifluoromethyl-phenyl)-ethylideneaminooxy]-butyl}-[1,3]dioxane-2-carboxylate;

Methyl-5-{4-[1-(4-fluoro-phenyl)-ethylideneaminooxy]-butyl}-2-methyl-[1,3]dioxane-2-carboxylate;

Methyl-5-{4-[1-(4-chloro-phenyl)-ethylideneaminooxy]-butyl}-2-methyl-[1,3]dioxane-2-carboxylate;

Methyl-5-{4-[1-(4-methanesulfonyl-phenyl)-ethylideneaminooxy]-butyl}-2-methyl-[1,3]dioxane-2-carboxylate;

Methyl-(2-methyl-5-[4-(1-m-tolyl-ethylideneaminooxy)-butyl]-[1,3]dioxane-)-2-carboxylate.

Methyl-5-{4-[1-(4-butyl-phenyl)-ethylideneaminooxy]-butyl}-2-methyl-[1,3]dioxane-2-carboxylate;

Methyl-2-methyl-5-[4-(1-p-tolyl-ethylideneaminooxy)-butyl]-[1,3]dioxane-2-carboxylate;

Methyl-2-methyl-5-{4-[1-(4-methylsulfanyl-phenyl)-ethylideneaminooxy]-butyl}-[1,3]dioxane-2-carboxylate;

Methyl-5-{4-[1-(4-ethyl-phenyl)-ethylideneaminooxy]-butyl}-2-methyl-[1,3]dioxane-2-carboxylate;

Methyl-5-{4-[1-(4-ethoxy-phenyl)-ethylideneaminooxy]-butyl}-2-methyl-[1,3]dioxane-2-carboxylate;

Methyl-5-{4-[1-(4-isopropoxy-phenyl)-ethylideneaminooxy]-butyl}-2-methyl-[1,3]dioxane-2-carboxylate;

Methyl-2-methyl-5-{4-[1-(4-phenoxy-phenyl)-ethylideneaminooxy]-butyl}-[1,3]dioxane-2-carboxylate;

Methyl-5-{4-[1-(4-isobutyl-phenyl)-ethylideneaminooxy]-butyl}-2-methyl-[1,3]dioxane-2-carboxylate;

Methyl-5-{4-[1-(4-methoxy-phenyl)-ethylideneaminooxy]-butyl}-2-methyl-[1,3]dioxane-2-carboxylate;

Methyl-5-{4-(1-biphenyl-4-yl-ethylideneaminooxy)-butyl]-2-methyl-[1,3]dioxane-2-carboxylate;

Methyl-5-{4-[1-(3-chloro-4-fluoro-phenyl)-ethylideneaminooxyl]-butyl}-2-methyl-[1,3]dioxane-2-carboxylate;

Methyl-5-{4-[1-(3,4-dimethyl-phenyl)-ethylideneaminooxyl]-butyl}-2-methyl-[1,3]dioxane-2-carboxylate;

Methyl-5-{5-[1-(3,4-dimethyl-phenyl)-ethylideneaminooxy]-pentyl}-2-methyl-[1,3]dioxane-2-carboxylate;

Methyl-5-{4-[1-(4-methoxy-3-methyl-phenyl)-ethylideneaminooxy]-butyl}-2-methyl-[1,3]dioxane-2-carboxylate;

Methyl-5-{4-[1-(3,4-dimethoxy-phenyl)-ethylideneaminooxy]-butyl}-2-methyl-[1,3]dioxane-2-carboxylate;

Methyl-5-{4-[1-(3-Fluoro-4-methoxy-phenyl)-ethylideneaminooxy]-butyl}-2-methyl-[1,3]dioxane-2-carboxylate;

Methyl-(5-{4-[1-(4-methoxy-phenyl)-propylideneaminooxy]-butyl}-2-methyl-[1,3]dioxane-2-carboxylate;

Methyl-{2-methyl-5-[4-(1-p-tolyl-propylideneaminooxy)-butyl]-[1,3]dioxane}-2-carboxylate;

Methyl-{2-methyl-5-[4-(1-pyridin-2-yl-ethylideneaminooxy)-butyl]-[1,3]dioxane-}-2-carboxylate;

Methyl-{2-methyl-5-[4-(1-pyridin-3-yl-ethylideneaminooxy)-butyl]-[1,3]dioxane-}-2-carboxylate;

Methyl-{2-methyl-5-[4-(1-pyridin-4-yl-ethylideneaminooxy)-butyl]-[1,3]dioxane-}-2-carboxylate;

Methyl-5-[4-(1-benzo[1,3]dioxol-5-yl-ethylideneaminooxy)-butyl]-2-methyl-[1,3]dioxane-2-carboxylate;

Methyl-2-methyl-5-[4-(1-thiophen-2-yl-ethylideneaminooxy)-butyl]-[1,3]dioxane-2-carboxylate;

Methyl-5-[4-(1-benzofuran-2-yl-ethylideneaminooxy)-butyl]-2-methyl-[1,3]dioxane-2-carboxylate;

Methyl-5-[5-(1-benzofuran-2-yl-ethylideneaminooxy)-pentyl]-2-methyl-[1,3]dioxane-2-carboxylate;

Methyl-5-{4-[1-(2,3-dimethyl-benzofuran-6-yl)-ethylideneaminooxy]-butyl}-2-methyl-[1,3]dioxane-2-carboxylate;

Methyl-2-methyl-5-{4-[1-(1-methyl-1H-indol-3-yl)-ethylideneaminooxy]-butyl}-[1,3]dioxane-2-carboxylate;

Methyl-2-methyl-5-[5-(1-naphthalen-2-yl-ethylideneaminooxy)-pentyl]-[1,3]dioxane-2-carboxylate;

Methyl-2-methyl-5-[4-(1-naphthalen-2-yl-ethylideneaminooxy)-butyl]-[1,3]dioxane-2-carboxylate;

Methyl-2-methyl-5-{4-[1-(5,6,7,8-tetrahydro-naphthalen-2-yl)-ethylideneaminooxy]-butyl}-[1,3]dioxane-2-carboxylate;

Methyl-5-{4-[1-(4-methoxymethoxy-phenyl)-ethylideneaminooxy]-butyl}-2-methyl-[1,3]dioxane-2-carboxylate;

Methyl-5-{4-[1-(4-hydroxy-phenyl)-ethylideneaminooxyl]-butyl}-2-methyl-[1,3]dioxane-2-carboxylate;

Methyl-5-{4-[1-(4-methanesulfortyloxy-phenyl)-ethylideneaminooxy]-butyl}-2-methyl-[1,3]dioxane-2-carboxylate;

Octyl-2-methyl-5-[4-(1-naphthalen-2-yl-ethylideneaminooxy)-butyl]-[1,3]dioxane-2-carboxylate;

2-Methyl-5-[4-(1-phenyl-ethylideneaminooxy)-butyl]-[1,3]dioxane-2-carboxylic acid and its pharmaceutically acceptable salts;

5-(4-Benzylideneaminooxy-butyl)-2-methyl-[1,3]dioxane-2-carboxylic acid and its pharmaceutically acceptable salts;

2-Methyl-5-{4-[1-(4-trifluoromethyl-phenyl)-ethylideneaminooxy]-butyl}-[1,3]dioxane-2-carboxylic acid and its pharmaceutically acceptable salts;

5-{4-[1-(4-Fluoro-phenyl)-ethylideneaminooxy]-butyl}-2-methyl-[1,3]dioxane-2-carboxylic acid and its pharmaceutically acceptable salts;

5-{4-[1-(4-Chloro-phenyl)ethylideneaminooxy]-butyl}-2-methyl-[1,3]dioxane-2-carboxylic acid and its pharmaceutically acceptable salts;

5-{4-[1-(4-Methanesulfonyl-phenyl)-ethylideneaminooxy]-butyl}-2-methyl-[1,3]dioxane-2-carboxylic acid and its pharmaceutically acceptable salts;

2-Methyl-5-[4-(1-p-tolyl-ethylideneaminooxy)-butyl]-[1,3]dioxane-2-carboxylic acid and its pharmaceutically acceptable salts;

5-{4-[1-(3-Chloro-4-fluoro-phenyl)-ethylideneaminooxy]-butyl}-2-methyl-[1,3]dioxane-2-carboxylic acid and its pharmaceutically acceptable salts;

5-{4-[1-(4-Butyl-phenyl)-ethylideneaminooxy]-butyl}-2-methyl-[1,3]dioxane-2-carboxylic acid and its pharmaceutically acceptable salts;

2-Methyl-5-{4-[1-(4-methylsulfanyl-phenyl)-ethylideneaminooxy]-butyl}-[1,3]dioxane-2-carboxylic acid and its pharmaceutically acceptable salts;

5-{4-[1-(4-Ethyl-phenyl)-ethylideneaminooxy]-butyl}-2-methyl-[1,3]dioxane-2-carboxylic acid and its pharmaceutically acceptable salts;

5-{4-[1-(3,4-Dimethyl-phenyl)-ethylideneaminooxy]-butyl}-2-methyl-[1,3]dioxane-2-carboxylic acid and its pharmaceutically acceptable salts;

5-{5-[1-(3,4-Dimethyl-phenyl)-ethylideneaminooxy]-pentyl}-2-methyl-[1,3]dioxane-2-carboxylic acid and its pharmaceutically acceptable salts;

5-{4-[1-(4-Ethoxy-phenyl)-ethylideneaminooxy]-butyl}-2-methyl-[1,3]dioxane-2-carboxylic acid and its pharmaceutically acceptable salts;

5-{4-[1-(4-Isopropoxy-phenyl)-ethylideneaminooxy]-butyl}-2-methyl-[1,3]dioxane-2-carboxylic acid and its pharmaceutically acceptable salts;

5-{4-[1-(4-Methoxy-3-methyl-phenyl)-ethylideneaminooxy]-butyl}-2-methyl-[1,3]dioxane-2-carboxylic acid and its pharmaceutically acceptable salts;

2-Methyl-5-{4-[1-(4-phenoxy-phenyl)-ethylideneaminooxy]-butyl}-[1,3]dioxane-2-carboxylic acid and its pharmaceutically acceptable salts;

5-{4-[1-(3,4-Dimethoxy-phenyl)-ethylideneaminooxy]-butyl}-2-methyl-[1,3]dioxane-2-carboxylic acid and its pharmaceutically acceptable salts;

5-{4-[1-(4-Isobutyl-phenyl)-ethylideneaminooxy]-butyl}-2-methyl-[1,3]dioxane-2-carboxylic acid;

5-{4-[1-(3-Fluoro-4-methoxy-phenyl)-ethylideneaminooxy]-butyl}-2-methyl-[1,3]dioxane-2-carboxylic acid and its pharmaceutically acceptable salts;

2-Methyl-5-[5-(1-naphthalen-2-yl-ethylideneaminooxy)-pentyl]-[1,3]dioxane-2-carboxylic acid and its pharmaceutically acceptable salts;

2-Methyl-5-[4-(1-naphthalen-2-yl-ethylideneaminooxy)-butyl]-[1,3]dioxane-2-carboxylic acid and its pharmaceutically acceptable salts;

2-Methyl-5-{4-[1-(5,6,7,8-tetrahydro-naphthalen-2-yl)-ethylideneaminooxy]-butyl}-[1,3]dioxane-2-carboxylic acid and its pharmaceutically acceptable salts;

5-{4-[1-(4-Hydroxy-phenyl)-ethylideneaminooxy]-butyl}-2-methyl-[1,3]dioxane-2-carboxylic acid and its pharmaceutically acceptable salts;

5-{4-[1-(4-Methoxy-phenyl)-ethylideneaminooxy]-butyl}-2-methyl-[1,3]dioxane-2-carboxylic acid and its pharmaceutically acceptable salts;

5-{4-[1-(4-Methanesulfonyloxy-phenyl)-ethylideneaminooxy]-butyl}-2-methyl-[1,3]dioxane-2-carboxylic acid and its pharmaceutically acceptable salts;

2-Methyl-5-[4-(1-thiophen-2-yl-ethylideneaminooxy)-butyl]-[1,3]dioxane-2-carboxylic acid and its pharmaceutically acceptable salts;

5-[4-(1-Benzo[1,3]dioxol-5-yl-ethylideneaminooxy)-butyl]-2-methyl-[1,3]dioxane-2-carboxylic acid and its pharmaceutically acceptable salts;

5-{4-(1-Biphenyl-4-yl-ethylideneaminooxy)-butyl}-2-methyl-[1,3]dioxane-2-carboxylic acid and its pharmaceutically acceptable salts;

2-Methyl-5-[4-(1-phenyl-pentylideneaminooxy)-butyl]-[1,3]dioxane-2-carboxylic acid and its pharmaceutically acceptable salts;

5-[4-(1-Benzofuran-2-yl-ethylideneaminooxy)-butyl]-2-methyl-[1,3]dioxane-2-carboxylic acid and its pharmaceutically acceptable salts;

5-[5-(1-Benzofuran-2-yl-ethylideneaminooxy)-pentyl]-2-methyl-[1,3]dioxane-2-carboxylic acid and its pharmaceutically acceptable salts;

5-{4-[1-(2,3-Dimethyl-benzofuran-6-yl)-ethylideneaminooxy]-butyl}-2-methyl-[1,3]dioxane-2-carboxylicacid and its pharmaceutically acceptable salts;

2-Methyl-5-{4-[1-(1-methyl-1H-indol-3-yl)-ethylideneaminooxy]-butyl}-[1,3]dioxane-2-carboxylic acid and its pharmaceutically acceptable salts;

2-Methyl-5-[4-(1-m-tolyl-ethylideneaminooxy)-butyl]-[1,3]dioxane-2-carboxylic acid and its pharmaceutically acceptable salts;

5-{4-[1-(4-Methoxy-phenyl)-propylideneaminooxy]-butyl}-2-methyl-[1,3]dioxane-2-carboxylic acid and its pharmaceutically acceptable salts;

2-Methyl-5-[4-(1-p-tolyl-propylideneaminooxy)-butyl]-[1,3]dioxane-2-carboxylic acid and its pharmaceutically acceptable salts;

2-Methyl-5-[4-(1-pyridin-2-yl-ethylideneaminooxy)-butyl]-[1,3]dioxane-2-carboxylic acid and its pharmaceutically acceptable salts;

2-Methyl-5-[4-(1-pyridin-3-yl-ethylideneaminooxy)-butyl]-[1,3]dioxane-2-carboxylic acid and its pharmaceutically acceptable salts;

2-Methyl-5-[4-(1-pyridin-4-yl-ethylideneaminooxy)-butyl]-[1,3]dioxane-2-carboxylic acid and its pharmaceutically acceptable salts;

2-Methyl-5-{4-[1-(5-methyl-furan-2-yl)-ethylideneaminooxy]-butyl}-[1,3]dioxane-2-carboxylic acid and its pharmaceutically acceptable salts.

The novel compounds of this invention may be prepared using the reactions and techniques as shown in scheme below and described in this section. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention.

Scheme:

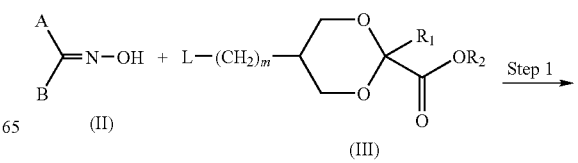

-continued

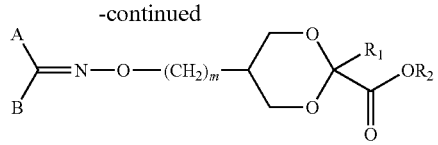

(I)

↓ Step II (I)

i. reacting compounds of general formula (II) where all symbols are as defined earlier with compounds of general formula (III), where all symbols are as defined earlier and L represents a suitable leaving group such as halogen, mesylate, tosylate, triflate & the like and $R_2$ represent alkyl group to yield compound of general formula (I) where all symbols are as defined earlier and $R_2$ represent alkyl group.
ii. hydrolysis of compound of general formula (I) wherein $R_2$ is alkyl and all other symbols are as defined earlier to yield further compound of general formula (I) wherein $R_2$ is H and all other symbols are as defined earlier.
iii. the compounds of formula (I) may optionally be converted to its pharmaceutically acceptable salts by techniques known in the art.

Step I: The compound of formula (I) may be prepared by reacting compound of formula (II) with compound of formula (III) under suitable conditions. The reaction may be carried out in presence of solvents such as acetone, tetrahydrofuran, dimethyl sulfoxide, dioxane, acetonitrile, dimethyl formamide, dimethoxy ethane, benzene, toluene, petroleum ether, heptane, hexane, 2-butanone, xylene, alcohols such as methanol, ethanol, propanol, butanol, iso-butanol, tert-butanol, pentanol and the like or mixtures thereof. Bases such as alkali metal carbonates such as $K_2CO_3$, $Na_2CO_3$, $CsCO_3$, and the like; or alkali metal hydroxides such as NaOH, KOH and the like, may be used during this reaction. Alkali metal hydrides such as NaH, KH can be used whenever solvent employed is not protic or contain carbonyl group. The reaction may be carried out at a temperature in the range 0° C. to reflux temperature of the solvent(s) used and the reaction time may range from 1 to 48 hours.

Step II: The compound of formula (I) may be hydrolysed to further compound of formula (I) using suitable base e.g., NaOH, LiOH, KOH and the like. Reaction may be conducted in suitable solvents e.g., alcohols like methanol, ethanol and the like, THF, water or the mixtures thereof. The reaction may be carried out at a temperature in the range 20° C. to reflux temperature of the solvent(s) used and the reaction time may range from 1 to 48 hours.

The invention is explained in greater detail by the examples given below, which are provided by way of illustration only and therefore should not be construed to limit the scope of the invention.

1H NMR spectral data given in the examples (vide infra) are recorded using a 300 MHz spectrometer (Bruker AVANCE-300) and reported in δ scale. Until and otherwise mentioned the solvent used for NMR is $CDCl_3$ using tetramethyl silane as the internal standard.

EXAMPLE 1

Methyl-2-methyl-5-[4-(1-phenyl-ethylideneaminooxy)-butyl]-[1,3]dioxane-2-carboxylate A mixture of 1-Phenyl-ethanone oxime (1.13 g), Methyl-5-(4-chloro-butyl)-2-methyl-[1,3]dioxane-2-carboxylate (prepared by processes known) (2.5 g) and cesium carbonate (4.0 g) in anhydrous dimethyl formamide was stirred at 60° C. for 18 hours in an inert atmosphere. The reaction mixture was cooled to ambient temperature, poured into ice cold water and extracted with ethyl-acetate. The combined organic extract was washed with water, brine solution, dried over sodium sulphate and evaporated under reduced pressure. Crude product was flash chromatographed over silica gel using 7% ethyl acetate in petroleum ether as eluent to obtain 2.5 g of pure product.

$^1$H NMR: 1.1 (2H, m), 1.4 (2H, m), 1.5 (3H, s), 1.7 (2H, m), 2.0 (1H, m), 2.2 (3H, s), 3.4 (2H, t, J=12.5 Hz), 3.8 (3H, s), 3.9 (2H, dd, J=12.0 & 4.6 Hz), 4.1 (2H, t, J=6.4 Hz), 7.3 (3H, m), 7.6 (2H, m). Yield: 85%

The following compounds are prepared by procedure similar to that described in example 1 with appropriate variations of reactants, reaction conditions and quantities of reagents.

EXAMPLE 2

Methyl-2-methyl-5-[4-(1-phenyl-pentylideneaminooxy)-butyl]-[1,3]dioxane-2-carboxylate $^1$H NMR: 0.9 (3H, t, J=7.2 Hz), 1.0 (2H, m), 1.4 (4H, m), 1.5 (5, m), 1.7 (2H, m), 2.0 (1H, m), 2.7 (2H, t, J=7.4 Hz), 3.4 (2H, t, J=11.5 Hz), 3.8 (3H, s), 4.0 (2H, dd, J=12.1 & 4.9 Hz), 4.2 (2H, t, J=6.4 Hz), 7.3 (3H, m), 7.6 (2H, m). Yield: 54%

EXAMPLE 3

Methyl-5-(4-benzylideneaminooxy-butyl)-2-methyl-[1,3]dioxane-2-carboxylate $^1$H NMR: 1.1 (2H, m), 1.4 (2H, m), 1.5 (3H, s), 1.73 (2H, m), 2.0 (1H, m), 3.4 (2H, t, J=11.7 Hz), 3.8 (3H, s), 3.9 (2H, dd, J=12.1 & 4.6 Hz), 4.1 (2H, t, J=6.4 Hz), 7.3 (3H, m), 7.5 (2H, m), 8.0 (1H, s). Yield: 82%

EXAMPLE 4

Methyl-2-methyl-5-{4-[1-(4-trifluoromethyl-phenyl)-ethylideneaminooxy]-butyl}-[1,3]dioxane-2-carboxylate $^1$H NMR: 1.0 (2H, m), 1.3 (2H, m), 1.5 (3H, s), 1.7 (2H, m), 2.0 (1H, m), 2.2 (3H, s), 3.4 (2H, t, J=11.8 Hz), 3.8 (3H, s), 4.0 (2H, dd, J=12.1 & 4.6 Hz), 4.2 (2H, t, J=6.5 Hz), 7.6 (2H, d, J=8.3 Hz), 7.7 (2H, d, J=8.2 Hz). Yield: 47%

EXAMPLE 5

Methyl-5-{4-[1-(4-fluoro-phenyl)-ethylideneaminooxy]-butyl}-2-methyl-[1,3]dioxane-2-carboxylate $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.5 Hz), 3.8 (3H, s), 3.9 (2H, dd, J=12.0 & 4.6 Hz), 4.1 (2H, t, J=6.4 Hz), 7.0 (2H, m), 7.6 (2H, m). Yield: 79%

EXAMPLE 6

Methyl-5-{4-[1-(4-chloro-phenyl)-ethylideneaminooxy]-butyl}-2-methyl-[1,3]dioxane-2-carboxylate $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.7 Hz), 3.8 (3H, s), 3.9 (2H, dd, J=12.0 & 4.6 Hz), 4.1 (2H, t, J=6.4 Hz), 7.3 (2H, dd, J=6.7 & 2.0 Hz), 7.6 (2H, dd, J=6.7 & 1.9 Hz). Yield: 86%

EXAMPLE 7

Methyl-5-{4-[1-(4-methanesulfonyl-phenyl)-ethylideneaminooxy]-butyl}-2-methyl-[1,3]dioxane-2-carboxylate $^1$H NMR: 1.12 (2H, m), 1.4 (2H, m), 1.5 (3H, s), 1.7 (2H, m), 2.0 (1H, m), 2.2 (3H, s), 3.0 (3H, s), 3.4 (2H, t, J=11.7 Hz), 3.8 (3H, s), 4.0 (2H, dd, J=12.0 & 4.6 Hz), 4.2 (2H, t, J=6.4 Hz), 7.8 (2H, dd, J=6.9 & 1.8 Hz), 7.9 (2H, d, J=8.5 Hz). Yield: 66%

EXAMPLE 8

Methyl-(2-methyl-5-[4-(1-m-tolyl-ethylideneaminooxy)-butyl]-[1,3]dioxane-)-2-carboxylate $^1$H NMR: 1.0 (2H, m), 1.37 (2H, m), 1.51 (3H, s), 1.67 (2H, m), 2.06 (1H, m), 2.2 (3H, s), 2.37 (3H, s), 3.4 (2H, t, J=11.5 Hz), 3.83 (3H, s), 3.98 (2H, dd, J=4.38 & 11.7 Hz), 4.1 (2H, t, J=6.43 Hz), 7.1 (2H, m), 7.4 (2H, m). Yield: 49%

EXAMPLE 9

Methyl-5-{4-[1-(4-butyl-phenyl)-ethylideneaminooxy]-butyl}-2-methyl-[1,3]dioxane-2-carboxylate $^1$H NMR: 0.91 (3H, t, J=7.26 Hz), 1.07 (2H, m), 1.36 (4H, m), 1.51 (3H, s), 1.60 (2H, m), 1.68 (2H, m), 2.04 (1H, m), 2.19 (3H, s), 2.61 (2H, t, J=7.53 Hz), 3.40 (2H, t, J=11.58 Hz), 3.82 (3H, s), 3.97 (2H, dd, J=11.88 & 4.5 Hz), 4.14 (2H, t, J=6.39 Hz), 7.16 (2H, d, J=8.1 Hz), 7.53 (2H, d, J=8.07 Hz). Yield: 46%

EXAMPLE 10

Methyl-2-methyl-5-[4-(1-p-tolyl-ethylideneaminooxy)-butyl]-[1,3]dioxane-2-carboxylate $^1$H NMR: 1.04-1.11 (2H, m), 1.37-1.40 (2H, m), 1.51 (3H, s), 1.64-1.71 (2H, m) 2.09 (1H, m), 2.19 (3H, s), 235 (3H, s), 3.40 (2H, t, J=11.61 Hz), 3.82 (3H, s), 3.96 (2H, dd, J=12.06 & 4.65 Hz), 4.14 (2H, t, J=7.42 Hz), 7.16 (2H, d, J=6.27 Hz), 7.52 (2H, d, J=8.13 Hz). Yield: 52%

EXAMPLE 11

Methyl-2-methyl-5-{4-[1-(4-methylsulfanyl-phenyl)-ethylideneaminooxy]-butyl}-[1,3]dioxane-2-carboxylate $^1$H NMR: 1.04-1.11 (2H, m), 1.34-1.42 (2H, m), 1.51 (3H, s), 1.66-1.71 (2H, m) 2.08 (1H, m), 2.38 (3H, s), 2.49 (3H, s), 3.40 (2H, t, J=11.67 Hz), 3.82 (3H, s), 3.96 (2H, dd, J=12.03 & 4.56 Hz), 4.14 (2H, t, J=6.42 Hz), 7.22 (2H, d, J=8.4 Hz), 7.55 (2H, d, J=8.4 Hz). Yield: 58%

EXAMPLE 12

Methyl-5-{4-[1-(4-ethyl-phenyl)-ethylidencaminooxyl]-butyl}-2-methyl-[1,3]dioxane-2-carboxylate $^1$H NMR: 1.06-1.11 (2H, m), 1.23 (3H, t, J=7.59 Hz), 1.34-1.40 (2H, m), 1.51 (3H, s), 1.69 (2H, m), 2.00 (1H, m), 2.20 (3H, s), 2.64 (2H, q, J=15.18 & 7.62 Hz), 3.40 (2H, t, J=11.76 Hz), 183 (3H, s), 3.97 (2H, dd, J=12.09 & 4.68 Hz), 4.14 (2H, t, J=6.45 Hz), 7.18 (2H, d, J=8.25 Hz), 7.55 (21-1, d, J=1.74 Hz). Yield: 54%

EXAMPLE 13

Methyl-5-{4-[1-(4-ethoxy-phenyl)-ethylideneaminooxy]-butyl}-2-methyl-[1,3]dioxane-2-carboxylate $^1$H NMR: 1.09 (2H, m), 1.3 (2H, m), 1.4 (3H, t, J=6.9 Hz), 1.51 (3H, m), 1.68 (2H, m), 2.04 (1H, m), 2.18 (3H, s), 3.40 (2H, t, J=11.67 Hz), 3.82 (3H, s), 3.96 (2H, dd, J=12.03 & 4.53 Hz), 4.04 (2H, q, J=13.98 & 6.99 Hz), 4.13 (2H, t, J=6.42 Hz), 6.86 (2H, d, J=8.76 Hz), 7.56 (2H, d, J=8.76 Hz). Yield: 38%

EXAMPLE 14

Methyl-5-{4-[1-(4-isopropoxy-phenyl)-ethylideneaminooxy]-butyl}-2-methyl-[1,3]dioxane-2-carboxylate $^1$H NMR: 1.05 (2H, m), 1.32 (3H, s), 1.34 (3H, s), 1.4 (2H, m), 1.51 (3H, s), 1.66 (2H, m), 2.04 (1H, m), 2.18 (3H, s), 3.40 (2H, t, J=11.64 Hz), 3.82 (3H, s), 3.96 (2H, dd, J=11.94 & 4.56 Hz), 4.13 (2H, t, J=6.42 Hz), 4.56 (1H, m), 6.86 (2H, d, J=8.76 Hz), 7.56 (2H, d, J=8.76 Hz). Yield: 47%

EXAMPLE 15

Methyl-2-methyl-5-{4-[1-(4-phenoxy-phenyl)-ethylideneaminooxy]-butyl}-[1,3]dioxane-2-carboxylate $^1$H NMR: 1.04-1.11 (2H, m), 1.34-1.40 (2H, m), 1.51 (3H, s), 1.64-1.73 (2H, m), 2.05 (1H, m), 2.20 (3H, s), 3.40 (2H, t, J=11.61 Hz), 3.83 (3H, s), 3.96 (2H, dd, J=12.09 & 4.65 Hz), 4.15 (2H, t, J=6.42 Hz), 6.97-7.03 (4H, m), 7.12 (1H, m), 7.32-7.37 (2H, m), 7.60 (2H, dd, J=6.81 & 2.01 Hz). Yield: 58%

EXAMPLE 16

Methyl-5-{4-[1-(4-isobutyl-phenyl)-ethylideneaminooxy]-butyl}-2-methyl-[1,3]dioxane-2-carboxylate $^1$H NMR: 0.88 (3H, s), 0.90 (3H, s), 1.06-1.11 (2H, m), 1.37 (2H, m), 1.51 (3H, s), 1.66-1.71 (2H, m), 1.84 (1H, m), 2.04 (1H, m), 2.20 (3H, s), 2.47 (2H, d, J=7.17 Hz), 3.40 (2H, t, J=11.67 Hz), 3.83 (3H, s), 3.97 (2H, dd, J=12.06 & 4.68 Hz), 4.15 (2H, t, J=6.24 Hz), 7.12-7.15 (2H, d, J=8.22 Hz), 7.52-7.55 (2H, d, J=8.22 Hz). Yield: 50%

EXAMPLE 17

Methyl-5-{4-[1-(4-methoxy-phenyl)-ethylideneaminooxy]-butyl}-2-methyl-[1,3]dioxane-2-carboxylate $^1$H NMR: 1.04-1.11 (2H, m), 1.34-1.40 (2H, m), 1.51 (3H, s), 1.64-1.71 (2H, m) 2.04 (1H, m), 2.19 (3H, s), 3.40 (2H, t, J=11.61 Hz), 3.82 (3H, s), 3.83 (3H, s) 3.96 (2H, dd, J=12.06 & 4.68 Hz), 4.13 (2H, t, J=6.42 Hz), 7.87-6.91 (2H, m), 7.56-7.60 (2H, m). Yield: 43%

EXAMPLE 18

Methyl-5-[4-(1-biphenyl-4-yl-ethylideneaminooxy)-butyl]-2-methyl-[1,3]dioxane-2-carboxylate $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.7 Hz), 3.8 (3H, s), 4.0 (2H, dd, J=12.1 & 4.7 Hz), 4.2 (2H, t, J=6.4 Hz), 7.3 (1H, m), 7.4 (2H, m), 7.6 (4H, m), 7.7 (2H, m). Yield: 67%

EXAMPLE 19

Methyl-5-{4-[1-(3-chloro-4-fluoro-phenyl)-ethylideneaminooxy]-butyl}-2-methyl-[1,3]dioxane-2-carboxylate $^1$H NMR: 1.04-1.12 (2H, m), 1.34-1.39 (2H, m), 1.51 (3H, s), 1.64-1.71 (2H, m), 2.04 (1H, m), 2.18 (3H, s), 3.40 (2H, t, J=11.7 Hz), 3.83 (3H, s), 3.96 (2H, dd, J=12.03 & 4.62 Hz), 4.15 (2H, t, J=6.45 Hz), 7.1 (1H, t, J=8.7 Hz), 7.47-7.53 (1H, m), 7.69-7.72 (1H, dd, J=7.17 & 2.4 Hz). Yield: 39%

EXAMPLE 20

Methyl-5-{4-[1-(3,4-dimethyl-phenyl)-ethylideneaminooxy]-butyl}-2-methyl-[1,3]dioxane-2-carboxylate $^1$H NMR: 1.04-1.11 (2H, m), 1.34-1.40 (2H, m), 1.51 (3H, s), 1.56-1.71 (2H, m), 2.05 (1H, m), 2.19 (3H, s), 2.26 (3H, s), 2.27 (3H, s), 3.40 (2H, t, J=11.73 Hz), 3.83 (3H, s), 3.96 (2H, dd, J=12.27 & 4.68 Hz), 4.14 (2H, t, J=6.45 Hz), 7.12 (1H, d, J=7.89 Hz), 7.33 (1H, dd, J=7.83 & 1.71 Hz), 7.41 (1H, s). Yield: 45%

EXAMPLE 21

Methyl-5-{5-[1-(3,4-dimethyl-phenyl)-ethylideneaminooxy]-pentyl}-2-methyl-[1,3]dioxane-2-carboxylate $^1$H NMR: 1.02-1.07 (2H, m), 1.25-1.37 (4H, m), 1.51 (3H, s), 1.64-1.71 (2H, m), 2.02 (1H, m), 2.19 (3H, s), 2.26 (3H, s), 2.27 (3H, s), 3.40 (2H, t, J=11.64 Hz), 3.83 (3H, s), 3.96 (2H, dd, J=12.03 & 4.62 Hz), 4.14 (2H, t, J=6.57 Hz), 7.12 (1H, d, J=7.86 Hz), 7.34 (1H, d, J=7.83 Hz), 7.41 (1H, s). Yield: 48%

EXAMPLE 22

Methyl-5-{4-[1-(4-methoxy-3-methyl-phenyl)-ethylideneaminooxy]-butyl}-2-methyl-[1,3]dioxane-2-carboxylate $^1$H NMR: 1.06-1.11 (2H, m), 1.34-1.40 (2H, m), 1.51 (3H, s), 1.57-1.71 (2H, m), 2.05 (1H, m), 2.18 (3H, s), 2.22 (3H, s), 3.40 (2H, t, J=11.73 Hz), 3.83 (3H, s), 3.84 (3H, s), 3.99 (2H, dd, J=1195 & 6.51 Hz), 4.13 (2H, t, J=6.45 Hz), 6.79 (1H, d, J=8.46 Hz), 7.39-7.45 (2H, m). Yield: 54%

EXAMPLE 23

Methyl-5-{4-[1-(3,4-dimethoxy-phenyl)-ethylideneaminooxy]-butyl}-2-methyl-[1,3]dioxance-2-carboxylate $^1$H NMR: 1.04-1.12 (2H, m), 1.33-1.40 (2H, m), 1.51 (3H, s), 1.64-1.71 (2H, m) 2.05 (1H, m), 2.19 (3H, s), 3.40 (2H, t, J=11.64 Hz), 3.83 (3H, s), 3.90 (3H, s), 3.92 (3H, s), 3.97 (2H, dd, J=12.06 & 4.68 Hz), 4.15 (2H, t, J=6.42 Hz), 6.85 (1H, d, J=8.52 Hz), 7.13 (1H, dd, J=8.37 & 2.04 Hz), 7.27 (1H, d, J=2.01 Hz). Yield: 47%

EXAMPLE 24

Methyl-5-{4-[1-(3-Fluoro-4-methoxy-phenyl)-ethylideneaminooxy]-butyl}-2-methyl-[1,3]dioxane-2-carboxylate $^1$H NMR: 1.04-1.11 (2H, m), 1.34-1.39 (2H, m), 1.51 (3H, s), 1.65-1.71 (2H, m), 2.04 (1H, m), 2.17 (3H, s), 3.40 (2H, t, J=11.67 Hz), 3.83 (3H, s), 3.90 (3H, s), 3.96 (2H, dd, J=12.06 & 4.65 Hz), 4.14 (2H, t, J=6.45 Hz), 6.93 (1H, t, J=8.64 Hz), 7.31-7.35 (1H, m), 7.42-7.47 (1H, dd, J=12.75 & 2.13 Hz). Yield: 50%

EXAMPLE 25

Methyl-(5-{4-[1-(4-methoxy-phenyl)-propylideneaminooxy]-butyl}-2-methyl-[1,3]dioxane-)-2-carboxylate $^1$H NMR: 1.1 (5H, m), 1.4 (2H, m), 1.51 (3H, s), 1.7 (2H, m), 2.1 (1H, m), 2.7 (2H, q, J=7.59 Hz), 3.4 (2H, t, J=11.67 Hz), 3.8 (6H, s), 3.98 (2H, dd, J=4.56 & 12.03 Hz), 4.1 (2H, t, J=6.36 Hz), 6.9 (2H, d, J=8.79 Hz), 7.55 (2H, d, J=8.79 Hz). Yield: 35%

EXAMPLE 26

Methyl-{2-methyl-5-[4-(1-p-tolyl-propylideneaminooxy)-butyl]-[1,3]dioxane}-2-carboxylate $^1$H NMR: 1.1 (5H, m), 1.4 (2H, m), 1.51 (3H, s), 1.7 (2H, m), 2.0 (1H, m), 2.35 (3H, s), 2.7 (2H, q, J=7.6 Hz), 3.4 (2H, t, J=11.56 Hz), 3.82 (3H, s), 3.95 (2H, dd, J=4.5 & 12.02 Hz), 4.1 (2H, t, J=6.3 Hz), 7.15 (2H, J=8.0 Hz), 7.5 (2H, J=8.0 Hz). Yield: 58%

EXAMPLE 27

Methyl-{2-methyl-5-[4-(1-pyridin-2-yl-ethylideneaminooxy)-butyl]-[1,3]dioxane-}-2-carboxylate $^1$H NMR: 1.0 (2H, m), 1.38 (2H, m), 1.51 (3H, s), 1.7 (2H, m), 2.0 (1H, m), 2.31 (3H, s), 3.4 (2H, t, J=11.42), 3.83 (3H, s), 3.9 (2H, dd, J=4.56 & 12.15 Hz), 4.2 (2H, t, J=6.47), 7.22

(1H, m), 7.6 (1H, m), 7.8 (1H, d, J=8.1 Hz), 8.6 (1H, d, J=4.71 Hz).

Yield: 49%

EXAMPLE 28

Methyl-{2-methyl-5-[4-(1-pyridin-3-yl-ethylidene-aminooxy)-butyl]-[1,3]dioxane-}-2-carboxylate $^1$H NMR: 1.0 (2H, m), 1.4 (2H, m), 1.51 (3H, s), 1.7 (2H, m), 2.0 (1H, m), 2.23 (3H, s), 3.4 (2H, t, J=11.4 Hz), 3.83 (3H, s), 3.9 (2H, dd, J=4.6 & 12.0 Hz), 4.2 (2H, t, J=6.47), 7.29 (1H, m), 7.96 (1H, dd, J=1.7 & 7.9 Hz), 8.57 (1H, d, J=4.7 Hz), 8.86 (1H, s).

Yield: 39%

EXAMPLE 29

Methyl-{2-methyl-5-[4-(1-pyridin-4-yl-ethylidene-aminooxy)-butyl]-[1,3]dioxane-}-2-carboxylate $^1$H NMR: 1.0 (2H, m), 1.35 (2H, m), 1.51 (3H, s), 1.7 (2H, m), 2.0 (1H, m), 2.19 (3H, s), 3.4 (2H, t, J=11.73 Hz), 3.82 (3H, s), 3.9 (2H, dd, J=4.44 & 11.79 Hz), 4.2 (2H, t, J=6.4 Hz), 7.5 (2H, d, J=6.0 Hz), 8.6 (2H, d, J=6.0 Hz). Yield: 38%

EXAMPLE 30

Methyl-5-[4-(1-benzo[1,3]dioxol-5-yl-ethylidene-aminooxy)-butyl]-2-methyl-[1,3]dioxane-2-carboxylate $^1$H NMR: 1.03-1.11 (2H, m), 1.31-1.39 (2H, m), 1.51 (3H, s), 1.63-1.70 (2H, m), 2.04 (1H, m), 2.16 (3H, s), 3.40 (2H, t, J=11.61 Hz), 3.83 (3H, s), 3.96 (2H, dd, J=12.06 & 4.65 Hz), 4.13 (2H, t, J=6.42 Hz), 5.97 (2H, s) 6.79 (1H, d, J=8.1 Hz), 7.08 (1H, dd, J=8.1 & 2.22 Hz), 7.19 (1H, d, J=1.65 Hz). Yield: 54%

EXAMPLE 31

Methyl-2-methyl-5-[4-(1-thiophen-2-yl-ethylidene-aminooxy)-butyl]-[1,3]dioxane-2-carboxylate $^1$H NMR: 1.03-1.11 (2H, m), 1.34-1.42 (2H, m), 1.51 (3H, s), 1.62-4.72 (2H, m) 2.04 (1H, m), 2.22 (3H, s), 3.40 (2H, t, J=11.41 Hz), 3.83 (3H, s), 3.97 (2H, dd, J=12 & 4.62 Hz), 4.21 (2H, t, J=6.39 Hz), 7.00 (1H, dd, J=5.07 & 3.75 Hz), 7.20 (1H, dd, J=4.56 & 1.05 Hz), 7.24 (1H, m). Yield: 46%

EXAMPLE 32

Methyl-5-[4-(1-benzofuran-2-yl-ethylideneami-nooxy)-butyl]-2-methyl-[1,3]dioxane-2-carboxylate $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.1 Hz), 3.8 (3H, s), 4.0 (2H, dd, J=12.1 & 4.6 Hz), 4.2 (2H, t, J=6.5 Hz), 6.9 (1H, s), 7.2-7.3 (2H, m), 7.5 (2H, m). Yield: 39%

EXAMPLE 33

Methyl-5-[5-(1-benzofuran-2-yl-ethylideneami-nooxy)-pentyl]-2-methyl-[1,3]dioxane-2-carboxylate $^1$H NMR: 1.0 (2H, m), 1.4 (4H, m), 1.5 (3H, s), 1.7 (2H, m), 2.0 (1H, m), 2.2 (3H, s), 3.4 (2H, t, J=11.7 Hz), 3.8 (3H, s), 3.9 (2H, dd, J=12.0 & 4.6 Hz), 4.2 (2H, t, J=6.6 Hz), 6.9 (1H, s), 7.2-7.3 (2H, m), 7.5 (2H, m). Yield: 62%

EXAMPLE 34

Methyl-5-{4-[1-(2,3-dimethyl-benzofuran-6-yl)-ethylideneaminooxy]-butyl}-2-methyl-[1,3]dioxane-2-carboxylate $^1$H NMR: 1.06 (2H, m), 1.41 (2H, m), 1.57 (3H, s), 1.74 (2H, m), 2.05 (1H, m), 2.14 (3H, s), 2.26 (3H, s), 2.38 (3H, s), 3.40 (2H, t, J=11.53 Hz), 3.83 (3H, s), 3.97 (2H, s), 4.17 (2H, t, J=6.13 Hz), 7.35 (1H, d, J=8.1 Hz), 7.51 (1H, d, J=8.01 Hz), 7.62 (1H, s). Yield: 39%

EXAMPLE 35

Methyl-2-methyl-5-{4-[1-(1-methyl-1H-indol-3-yl)-ethylideneaminooxy]-butyl}-[1,3]dioxane-2-carboxylate $^1$H NMR: 1.05-1.13 (2H, m), 1.35-1.46 (2H, m), 1.50 (3H, s), 1.70-1.77 (2H, m), 2.05 (1H, m), 2.23 (3H, s), 3.40 (2H, t, J=11.46 Hz), 3.79 (3H, s), 3.82 (3H, s), 3.97 (2H, dd, J=11.95 & 4.032 Hz), 4.19 (2H, t, J=6.42 Hz), 7.17-7.31 (4H, m), 8.27 (1H, d, J=7.71 Hz).

Yield: 47%

EXAMPLE 36

Methyl-2-methyl-5-[5-(1-naphthalen-2-yl-ethylide-neaminooxy)-pentyl]-[1,3]dioxane-2-carboxylate $^1$H NMR: 1.06 (2H, m), 1.25-1.41 (4H, m), 1.51 (3H, s), 1.73 (2H, m), 2.04 (1H, m), 2.32 (3H, s), 3.40 (2H, t, J=11.76 Hz), 3.82 (3H, s), 3.96 (2H, dd, J=12.06 & 4.59 Hz), 4.21 (2H, t, J=6.57 Hz), 7.47 (2H, m), 7.78-7.92 (4H, m), 7.98 (1H, s). Yield: 33%

EXAMPLE 37

Methyl-2-methyl-5-[4-(1-naphthalen-2-yl-ethylide-neaminooxy)-butyl]-[1,3]dioxane-2-carboxylate $^1$H NMR: 1.06-1.14 (2H, m), 1.40 (2H, m), 1.51 (3H, s), 1.71-1.75 (2H, m) 2.06 (1H, m), 2.33 (3H, s), 3.37-3.51 (2H, t, J=11.6 Hz), 3.82 (3H, s), 4.00 (2H, q, J=11.91 & 4.56 Hz), 4.21 (2H, t, J=6.39 Hz), 7.48 (2H, m), 7.79-7.92 (4H, m), 7.99 (1H, m).

Yield: 52%

EXAMPLE 38

Methyl-2-methyl-5-{4-[1-(5,6,7,8-tetrahydro-naph-thalen-2-yl)-ethylideneaminooxy]-butyl}-[1,3]diox-ane-2-carboxylate $^1$H NMR: 1.06-1.11 (2H, m), 1.38 (2H, m), 1.51 (3H, s), 1.68 (2H, m), 1.76-1.81 (4H, m), 2.04 (1H, m), 2.18 (3H, s), 2.77 (4H, m), 3.40 (2H, t, J=11.61 Hz), 3.83 (3H, s), 3.96 (2H, dd, J=11.91 & 4.47 Hz), 4.14 (2H, t, J=6.45 Hz), 7.03-7.06 (1H, d, J=7.74 Hz), 7.32-7.35 (2H, m). Yield: 50%

EXAMPLE 39

Methyl-5-{4-[1-(4-methoxymethoxy-phenyl)-ethylideneaminooxy]-butyl}-2-methyl-[1,3]dioxane-2-carboxylate $^1$H NMR: 1.09 (2H, m), 1.34-1.39 (2H, m), 1.51 (3H, s), 1.66-1.71 (2H, m) 2.04 (1H, m), 2.18 (3H, s), 3.40 (2H, t, J=11.8 Hz), 3.47 (3H, s), 3.83 (3H, s), 3.96 (2H, dd, J=12.06 & 4.65 Hz), 4.13 (2H, t, J=6.45 Hz), 5.19 (2H, s), 6.99-7.04 (2H, m) 7.54-7.58 (2H, m)

Yield: 47%

EXAMPLE 40

Methyl-5-{4-[1-(4-hydroxy-phenyl)-ethylideneaminooxy]-butyl}-2-methyl-[1,3]dioxane-2-carboxylate To a solution of Methyl-5-{4-[1-(4-methoxymethoxy-phenyl)-ethylideneaminooxy]-butyl}-2-methyl-[1,3]dioxane-2-carboxylate (prepared as per example 39) (1.5 g) in isopropyl alcohol was added concentrated hydrochloric acid and the reaction mixture was stirred at 50° C. for about 20 hours. Reaction mixture was cooled to ambient temperature and solvent was evaporated under reduced pressure on a rotavapor. Water was added to the residue and extracted with ethyl acetate. The combined organic extract was washed with water, brine solution, dried over sodium sulphate and evaporated under reduced pressure on a rotavapor. Crude product was flash chromatographed over silica gel using 15% ethyl acetate in petroleum ether as eluent to obtain 200 mg of pure product.

$^1$H NMR: 1.04-1.11 (2H, m), 1.32-1.42 (2H, m), 1.51 (3H, s), 1.63-1.70 (2H, m) 2.04 (1H, m), 2.18 (3H, s), 3.40 (2H, t, J=11.8 Hz), 3.83 (3H, s), 3.96 (2H, dd, J=12.06 & 4.68 Hz), 4.13 (2H, t, J=6.42 Hz), 6.81 (2H, dd, J=6.69 & 2.01 Hz), 7.54 (2H, dd, J=6.69 & 1.95 Hz). Yield: 15%

EXAMPLE 41

Methyl-5-{4-[1-(4-methanesulfonyloxy-phenyl)-ethylideneaminooxy]-butyl}-2-methyl-[1,3]dioxane-2-carboxylate To an ice cold solution of Methyl-5-{4-[1-(4-hydroxy-phenyl)-ethylideneaminooxy]-butyl}-2-methyl-[1,3]dioxane-2-carboxylate (prepared as per example 40) (200 mg) in anhydrous dichloromethane were added triethyl amine (82 mg) and methane sulfonyl chloride (75 mg) and the reaction mixture was stirred at the same temperature for about an hour. Reaction mixture was diluted with dichloromethane, washed with water, dried over sodium sulphate and evaporated under, reduced pressure on a rotavapor. Crude product was flash chromatographed over silica gel using 20% ethyl acetate in petroleum ether as eluent to obtain 200 mg of pure product.

$^1$H NMR: 1.04-1.12 (2H, m), 1.34-1.42 (2H, m), 1.51 (3H, s), 1.56-1.71 (2H, m) 2.04 (1H, m), 2.21 (3H, s), 3.14 (3H, s), 3.40 (2H, t, J=11.8 Hz), 3.83 (3H, s), 3.96 (2H, dd, J=12.06 & 4.68 Hz), 4.16 (2H, t, J=6.48 Hz), 7.27-7.29 (2H, m), 7.67-7.70 (2H, m). Yield: 83%

EXAMPLE 42

2-Methyl-5-[4-(1-phenyl-ethylideneaminooxy)-butyl]-[1,3]dioxane-2-carboxylic Acid To a solution of. Methyl-2-methyl-5-[4-(1-phenyl-ethylideneaminooxy)-butyl]-[1,3]dioxane-2-carboxylate (prepared as per example 1) (1.38 g) in a mixture of tetrahydrofuran and methanol was added another solution of LiOH.H$_2$O (332 mg) in water and the reaction mixture was stirred at ambient temperature for about 18 hours. Solvent was evaporated under reduced pressure, water was added to the residue, acidified with 1N HCl to pH 6 and extracted with ethyl acetate. The combined organic extract was washed with water, brine solution, dried over sodium sulphate and evaporated under reduced pressure. Crude product was chromatographed (flash) over silica-gel using 25% ethyl acetate in hexane as an eluent to obtain 1 g of pure product.

$^1$H NMR: 1.1 (2H, m), 1.4 (2H, m), 1.5 (3H, s), 1.7 (2H, m), 2.0 (1H, m), 2.2 (3H, s), 3.4 (2H, t, J=11.5 Hz), 4.0 (2H, dd, J=12.0 & 4.5 Hz), 4.1 (2H, t, J=6.4 Hz), 7.3 (3H, m), 7.6 (2H, m). Yield: 79%

The following compounds are prepared by procedure similar to that described in example 42 with appropriate variations of reactants, reaction conditions and quantities of reagents.

EXAMPLE 43

5-(4-Benzylideneaminooxy-butyl)-2-methyl-[1,3]dioxane-2-carboxylic Acid $^1$H NMR: 1.1 (2H, m), 1.4 (2H, m), 1.5 (3H, s), 1.73 (2H, m), 2.0 (1H, m), 3.4 (2H, t, J=11.6 Hz), 4.0 (2H, dd, J=11.9 & 4.5 Hz), 4.1 (2H, t, J=6.4 Hz), 7.3 (3H, m), 7.5 (2H, m), 8.0 (1H, s). Yield: 96%

EXAMPLE 44

2-Methyl-5-{4-[1-(4-trifluoromethyl-phenyl)-ethylideneaminooxy]-butyl}-[1,3]dioxane-2-carboxylic Acid $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.6 Hz), 4.0 (2H, dd, & 4.7 Hz), 4.1 (2H, t, J=6.4 Hz), 7.6 (2H, t, J=8.2 Hz), 7.7 (2H, d, J=8.0 Hz). Yield: 97%

EXAMPLE 45

5-{4-[1-(4-Fluoro-phenyl)-ethylideneaminooxy]-butyl}-2-methyl-[1,3]dioxane-2-carboxylic Acid $^1$H NMR: 1.1 (2H, m), 1.4 (2H, m), 1.5 (3H, s), 1.7 (2H, m), 2.0 (1H, m), 2.2 (3H, s), 3.4 (2H, t, J=11.6 Hz), 4.0 (2H, dd, J=11.9 & 4.5 Hz), 4.1 (2H, t, J=6.4 Hz), 7.0 (2H, t, J=8.6 Hz), 7.6 (2H, m). Yield: 83%

EXAMPLE 46

5-{4-[1-(4-Chloro-phenyl)-ethylideneaminooxy]-butyl}-2-methyl-[1,3]dioxane-2-carboxylic Acid $^1$H NMR: 1.1 (2H, m), 1.3 (2H, m), 1.5 (3H, s), 1.7 (2H, m), 2.0 (1H, m), 2.2 (3H, s), 3.5 (2H, t, J=11.5 Hz), 4.0 (2H, m), 4.1 (2H, t, J=6.3 Hz), 7.3 (2H, d, J=8.5 Hz), 7.6 (2H, d, J=8.5 Hz). Yield: 79%

EXAMPLE 47

5-{4-[1-(4-Methanesulfonyl-phenyl)-ethylideneaminooxy]-butyl}-2-methyl-[1,3]dioxane-2-carboxylic Acid $^1$H NMR: 1.1 (2H, m), 1.4 (2H, m), 1.5 (3H, s), 1.7 (2H, m), 2.0 (1H, m), 2.2 (3H, s), 3.0 (3H, s), 3.4 (2H, t, J=11.6 Hz), 4.0 (2H, dd, J=11.9 & 4.4 Hz), 4.2 (2H, t, J=6.4 Hz), 7.8 (2H, d, J=8.5 Hz), 7.9 (2H, d, J=8.5 Hz). Yield: 80%

EXAMPLE 48

2-Methyl-5-[4-(1-p-tolyl-ethylideneaminooxy)-butyl]-[1,3]dioxane-2-carboxylic Acid $^1$H NMR: 1.07-1.14 (2H, m), 1.33-1.41 (2H, m), 1.52 (3H, s), 1.64-1.72 (2H, m) 2.05 (1H, m), 2.19 (3H, s), 2.35 (3H, s), 3.47 (2H, m), 3.99 (2H, dd, J=12.03 & 4.56 Hz), 4.15 (2H, t, J=6.45 Hz), 7.16 (2H, d, J=8.07 Hz), 7.52 (2H, d, J=8.19 Hz). Yield: 22%

EXAMPLE 49

5-{4-[1-(3-Chloro-4-fluoro-phenyl)-ethylideneaminooxy]-butyl}-2-methyl-[1,3]dioxane-2-carboxylic Acid $^1$H NMR: 1.07-1.15 (2H, m), 1.35 (2H, m), 1.56 (3H, s), 1.65-1.71 (2H, m), 2.05 (1H, m), 2.18 (3H, s), 3.43-3.57 (2H, m), 3.99 (2H, dd, J=11.48 & 4.56 Hz), 4.16 (2H, t, J=6.42 Hz), 7.12 (1H, m), 7.47-7.69 (1H, m), 7.70 (1H, dd, J=7.08 & 2.16 Hz).
Yield: 89%

EXAMPLE 50

5-{4-[1-(4-Butyl-phenyl)-ethylideneaminooxy]-butyl}-2-methyl-[1,3]dioxane-2-carboxylic Acid $^1$H NMR: 0.91 (3H, t, J=7.29 Hz), 1.12 (2H, m), 1.36 (4H, m), 1.56-1.61 (5H, s), 1.69 (2H, m), 2.04 (1H, m), 2.17 (3H, s), 2.61 (2H, t, J=7.53 Hz), 3.46 (2H, t, J=11.46 Hz), 3.99 (2H, dd, J=11.88 & 4.5 Hz), 4.15 (2H, t, J=33 Hz), 7.16 (2H, d, J=8.07 Hz), 7.53 (2H, d, J=8.04 Hz). Yield: 98%

EXAMPLE 51

2-Methyl-5-{4-[1-(4-methylsulfanyl-phenyl)-ethylideneaminooxy]-butyl}-[1,3]dioxane-2-carboxylic Acid $^1$H NMR: 1.07-1.15 (2H, m), 1.33-1.43 (2H, m), 1.57 (3H, s), 1.65-1.72 (2H, m) 2.06 (1H, m), 219 (3H, s), 2.49 (3H, s), 3.46 (2H, t, 11.52 Hz), 3.99 (2H, dd, J=12.06 & 4.68 Hz), 4.15 (2H, t, J=6.42 Hz), 7.22 (2H, d J=8.46 Hz), 7.54-7.57 (2H, d, J=8.43 Hz). Yield: 76%

EXAMPLE 52

5-{4-[1-(4-Ethyl-phenyl)-ethylideneaminooxy]-butyl}-2-methyl-[1,3]dioxane-2-carboxylic Acid $^1$H NMR: 1.09-1.14 (2H, m), 1.22 (3H, t, J=7.59 Hz), 1.38 (2H, m), 1.56 (3H, s), 1.64-1.74 (2H, m), 2.05 (1H, m), 2.20 (3H, s), 2.63 (2H, q, J=15.06 & 7.53 Hz), 3.46 (2H, t, J=10.2 Hz), 3.99 (2H, dd, J=11.46 & 4.23 Hz), 4.15 (2H, t, J=6.36 Hz), 7.18 (2H, d, J=8.07 Hz), 7.54 (2H, d, J=8.16 Hz). Yield: 91%

EXAMPLE 53

5-{4-[1-(3,4-Dimethyl-phenyl)-ethylideneaminooxy]-butyl}-2-methyl-[1,3]dioxane-2-carboxylic Acid $^1$H NMR: 1.07-1.14 (2H, m), 1.35-1.42 (2H, m), 1.56 (3H, s), 1.67-1.71 (2H, m), 2.05 (1H, m), 2.19 (3H, s), 2.26 (3H, s), 2.27 (3H, s), 3.46 (2H, t, J=10.2 Hz), 3.99 (2H, dd, J=11.46 & 4.23 Hz), 4.15 (2H, t, J=6.42 Hz), 7.12 (1H, d, J=7.83 Hz), 7.32-7.36 (1H, m), 7.60 (1H, m). Yield: 84%

EXAMPLE 54

5-{5-[1-(3,4-Dimethyl-phenyl)-ethylideneaminooxy]-pentyl}-2-methyl-[1,3]dioxane-2-carboxylic Acid $^1$H NMR: 1.05-1.10 (2H, m), 1.28-1.38 (4H, m), 1.56 (3H, s), 1.69 (2H, m), 2.03 (1H, m), 2.19 (3H, s), 2.26 (3H, s), 2.27 (3H, s), 3.45 (2H, t, J=11.8 Hz), 3.99 (2H, dd, J=11.96 & 4.53 Hz), 4.15 (2H, t, J=6.51 Hz), 7.12 (1H, d, J=7.86 Hz), 7.33 (1H, d, J=7.98 Hz), 7.41 (1H, s). Yield: 89%

EXAMPLE 55

5-{4-[1-(4-Ethoxy-phenyl)-ethylideneaminooxy]-butyl}-2-methyl-[1,3]dioxane-2-carboxylic Acid $^1$H NMR: 1.06-1.14 (2H, m), 1.25-1.43 (5H, m), 1.56 (3H, s), 1.68 (2H, m), 2.04 (1H, m), 2.18 (3H, s), 3.46 (2H, t, J=11.52 Hz), 3.96-4.08 (4H, m), 4.13 (2H, t, J=6.39 Hz), 6.86 (2H, d, J=8.79 Hz), 7.56 (2H, d, J=8.79 Hz). Yield: 90%

EXAMPLE 56

5-{4-[1-(4-Isopropoxy-phenyl)-ethylideneaminooxy]-butyl}-2-methyl-[1,3]dioxane-2-carboxylic Acid $^1$H NMR: 0.86 (2H, m), 1.06-1.24 (8H, m), 1.56 (3H, s), 1.66 (2H, m), 2.04 (1H, m), 2.18 (3H, s), 3.46 (2H, t, J=10.59 Hz), 3.96 (2H, dd, J=11.70 & 4.56 Hz), 4.13 (2H, t, J=6.36 Hz), 4.56 (1H, m), 6.86 (2H, d, J=8.58 Hz), 7.56 (2H, d, J=8.58 Hz). Yield: 87%

EXAMPLE 57

5-{4-[1-(4-Methoxy-3-methyl-phenyl)-ethylideneaminooxy]-butyl}-2-methyl-[1,3]dioxane-2-carboxylic Acid $^1$H NMR: 1.09-1.14 (2H, m), 1.35-1.43 (2H, m), 1.56 (3H, s), 1.64-1.74 (2H, m), 2.05 (1H, m), 2.18 (3H, s), 2.22 (3H, m), 3.46 (2H, t, J=10.32 Hz), 3.84 (3H, s), 3.99 (2H, dd, J=11.88 & 4.50 Hz), 4.14 (2H, t, J=6.39 Hz), 6.80 (1H, d, J=8.46 Hz), 7.44 (1H, dd, J=8.46 & 2.06 Hz), 7.45 (1H, m). Yield: 82%

EXAMPLE 58

2-Methyl-5-{4-[1-(4-phenoxy-phenyl)-ethylideneaminooxy]-butyl}-[1,3]dioxane-2-carboxylic Acid $^1$H NMR: 1.09-1.14 (2H, m), 1.36-1.41 (2H, m), 1.56 (3H, s), 1.65-1.74 (2H, m), 2.05 (1H, m), 2.20 (3H, s), 3.46 (2H, m), 3.99 (2H, dd, J=12.03 & 4.59 Hz), 4.15 (2H, t, to J=6.39 Hz), 6.97-7.035 (4H, m), 7.12 (1H, d, J=7.35 Hz), 7.33 (2H, m), 7.60 (2H, d, J=6.81 & 2.01 Hz). Yield: 78%

EXAMPLE 59

5-{4-[1-(3,4-Dimethoxy-phenyl)-ethylideneaminooxy]-butyl}-2-methyl-[1,3]dioxane-2-carboxylic Acid $^1$H NMR: 1.09-1.15 (2H, m), 1.36-1.41 (2H, m), 1.56 (3H, s), 1.67-1.72 (2H, m) 2.05 (1H, m), 2.19 (3H, s), 3.46 (2H, t, J=11.58 Hz), 3.89 (3H, s), 3.92 (3H, s), 3.99 (2H, dd, J=12.06 & 4.50 Hz), 4.15 (2H, t, J=6.42 Hz), 6.85 (1H, d, J=8.4 Hz), 7.13 (1H, dd, J=8.37 & 2.04 Hz), 7.27 (1H, d, J=2.01 Hz). Yield: 81%

EXAMPLE 60

5-{4-[1-(4-Isobutyl-phenyl)-ethylideneaminooxy]-butyl}-2-methyl-[1,3]dioxane-2-carboxylic Acid $^1$H NMR: 0.88 (3H, s), 0.90 (3H, s), 1.09-1.14 (2H, m), 1.38 ((2H, m), 1.56 (3H, s), 1.62 (2H, m), 1.85 (1H, m) 2.01 (1H, m), 2.20 (3H, s), 2.47 (2H, d, J=7.17 Hz), 3.46 (2H, t, J=9.48 Hz), 3.99 (2H, dd, J=12.06 & 4.56 Hz), 4.15 (2H, t, J=6.45 Hz), 7.12 (2H, d, J=8.28 Hz), 7.53 (2H, d, J=8.16 Hz). Yield: 97%

EXAMPLE 61

5-{4-[1-(3-Fluoro-4-methoxy-phenyl)-ethylideneaminooxy]-butyl}-2-methyl-[1,3]dioxane-2-carboxylic Acid $^1$H NMR: 1.07-1.14 (2H, m), 1.33-1.40 (2H, m), 1.56 (3H, s), 1.64-1.73 (2H, m), 2.05 (1H, m), 2.17 (3H, s), 3.46 (2H, t, J=11.51), 3.90 (3H, s), 3.99 (2H, dd, J=12.06 & 4.59 Hz), 4.14 (2H, t, J=6.42 Hz), 6.91 (1H, m), 731-7.35 (1H, m), 7.42-7.47 (1H, dd, J=12.75 & 2.13 Hz). Yield: 90%

EXAMPLE 62

2-Methyl-5-[5-(1-naphthalen-2-yl-ethylideneaminooxy)-pentyl]-[1,3]dioxane-2-carboxylic Acid $^1$H NMR: 1.03-1.10 (2H, m), 1.32-1.40 (4H, m), 1.55 (3H, s), 1.71 (2H, m), 2.04 (1H, m), 2.32 (3H, s), 3.49 (2H, t, J=7.92 Hz), 3.98 (2H, dd, J=11.64 & 4.38 Hz), 4.21 (2H, t, J=6.54 Hz), 7.45-7.50 (2H, m), 7.77-7.91 (4H, m), 7.98 (1H, s). Yield: 53%

EXAMPLE 63

2-Methyl-5-[4-(1-naphthalen-2-yl-ethylideneaminooxy)-butyl]-[1,3]dioxane-2-carboxylic Acid $^1$H NMR: 1.09-1.16 (2H, m), 1.36-1.46 (2H, m), 1.57 (3H, s), 1.69-1.78 (2H, m) 2.07 (1H, m), 2.33 (3H, s), 3.47 (2H, t, J=11.16 Hz), 4.0 (2H, dd, J=11.82 & 4.68 Hz), 4.21 (2H, t, J=6.36 Hz), 7.48 (2H, dd, J=6.12 & 3.21 Hz), 7.78-7.91 (4H, m), 7.99 (1H, m).
Yield: 82%

EXAMPLE 64

2-Methyl-5-{4-[1-(5,6,7,8-tetrahydro-naphthalen-2-yl)-ethylideneaminooxy]-butyl}-[1,3]dioxane-2-carboxylic Acid $^1$H NMR: 1.09-1.14 (2H, m), 1.35-1.40 (2H, m), 1.56 (3H, s), 1.64-1.71 (2H, m), 1.76-1.81 (4H, m), 2.05 (1H, m), 2.18 (3H, s), 2.77 (4H, m), 3.46 (2H, t, J=11.55 Hz), 3.99 (2H, dd, J=12.00 & 4.67 Hz), 4.14 (2H, t, J=6.45 Hz), 7.03-7.06 (1H, d, J=7.8 Hz), 7.32 (1H, s), 7.34 (1H, s). Yield: 77%

EXAMPLE 65

5-{4-[1-(4-Hydroxy-phenyl)-ethylideneaminooxy]-butyl}-2-methyl-[1,3]dioxane-2-carboxylic Acid $^1$H NMR: 0.85 (2H, m), 1.25 (2H, m), 1.52 (3H, s), 1.67 (2H, m), 2.04 (1H, m), 2.16 (3H, s), 3.51 (2H, t, J=11.70 Hz), 3.94 (2H, dd, J=11.88 & 4.5 Hz), 4.11 (2H, t, J=6.42 Hz), 6.82 (2H, d, J=8.7 Hz), 7.49 (2H, m). Yield: 90%

EXAMPLE 66

5-{4-[1-(4-Methoxy-phenyl)-ethylideneaminooxy]-butyl}-2-methyl-[1,3]dioxane-2-carboxylic Acid $^1$H NMR: 1.06-1.14 (2H, m), 1.33-1.43 (2H, m), 1.56 (3H, s), 1.64-1.71 (2H, m) 2.05 (1H, m), 2.18 (3H, s), 3.46 (2H, t, J=11.52 Hz), 3.82 (3H, s), 3.99 (2H, dd, J=12.06 & 4.68 Hz), 4.13 (2H, t, J=6.42 Hz), 7.85-6.90 (2H, m), 7.55-7.60 (2H, m). Yield: 94%

EXAMPLE 67

5-{4-[1-(4-Methanesulfonyloxy-phenyl)-ethylideneaminooxy]-butyl}-2-methyl-[1,3]dioxane-2-carboxylic Acid $^1$H NMR: 1.13 (2H, m), 1.33-1.43 (2H, m), 1.56 (3H, s), 1.65-1.72 (2H, m) 2.01 (1H, m), 2.19 (3H, s), 3.16 (3H, s), 3.40-3.49 (2H, m), 3.99 (2H, dd, J=12.06 & 4.68 Hz), 4.18 (2H, t, J=5.04 Hz), 7.29-7.39 (2H, m), 7.68-7.71 (2H, d, J=6.78 & 2.01 Hz).
Yield: 34%

EXAMPLE 68

2-Methyl-5-[4-(1-thiophen-2-yl-ethylideneaminooxy)-butyl]-[1,3]dioxane-2-carboxylic Acid $^1$H NMR: 1.09-1.12 (2H, m), 1.38 (2H, m), 1.57 (3H, s), 1.65-1.70 (2H, m) 2.07 (1H, m), 2.33 (3H, s), 3.47 (2H, t, J=11.37 Hz), 4.0 (2H, dd, J=11.85 & 4.05 Hz), 4.13 (2H, t, J=6.33 Hz), 7.01 (1H, m), 7.19-7.24 (2H, m). Yield: 85%

EXAMPLE 69

5-[4-(1-Benzo[1,3]dioxol-5-yl-ethylideneaminooxy)-butyl]-2-methyl-[1,3]dioxane-2-carboxylic acid $^1$H NMR: 1.07-1.14 (2H, m), 1.35-1.43 (2H, m), 1.57 (3H, s), 1.60-1.71 (2H, m), 2.05 (1H, m), 2.17 (3H, s), 3.47 (2H, t, J=11.15 Hz), 3.99 (2H, dd, J=12.03 & 4.59 Hz), 4.13 (2H, t, J=6.39 Hz), 5.97 (2H, s), 6.79 (1H, d, J=8.16 Hz), 7.08 (1H, dd, J=8.1 & 1.77 Hz), 7.20 (1H, d, J=1.68 Hz). Yield: 84%

EXAMPLE 70

5-[4-(1-Biphenyl-4-yl-ethylideneaminooxy)-butyl]-2-methyl-[1,3]dioxane-2-carboxylic Acid ¹H NMR: 1.1 (2H, m), 1.4 (2H, m), 1.5 (3H, s), 1.7 (2H, m), 2.0 (1H, m), 2.2 (3H, s), 3.5 (2H, t, J=11.4 Hz), 4.0 (2H, dd, J=11.5 & 3.9 Hz), 4.2 (2H, t, J=6.3 Hz), 7.3 (1H, m), 7.4 (2H, m), 7.6 (4H, m), 7.7 (2H, m). Yield: 74%

EXAMPLE 71

2-Methyl-5-[4-(1-phenyl-pentylideneaminooxy)-butyl]-[1,3]dioxane-2-carboxylic Acid ¹H NMR: 0.93 (3H, t, J=7.2 Hz), 1.1 (2H, m), 1.4 (4H, m), 1.5 (2H, m), 1.57 (3H, s), 1.7 (2H, m), 2.0 (1H, m), 2.7 (2H, t, J=7.4 Hz), 3.4 (2H, t, J=11.4 Hz), 4.0 (2H, dd, J=11.8 & 4.5 Hz), 4.1 (2H, t, J=6.3 Hz), 7.3 (2H, m), 7.6 (3H, m). Yield: 96%

EXAMPLE 72

5-[4-(1-Benzofuran-2-yl-ethylideneaminooxy)-butyl]-2-methyl-[1,3]dioxane-2-carboxylic acid ¹H NMR: 1.1 (2H, m), 1.4 (2H, m), 1.5 (3H, s), 1.7 (2H, m), 2.0 (1H, m), 2.2 (3H, s), 3.5 (2H, t, J=11.6 Hz), 4.0 (2H, dd, J=11.9 & 4.5 Hz), 4.2 (2H, t, J=6.4 Hz), 6.9 (1H, s), 7.2-7.3 (2H, m), 7.5 (2H, m). Yield: 50%

EXAMPLE 73

5-[5-(1-Benzofuran-2-yl-ethylideneaminooxy)-pentyl]-2-methyl-[1,3]dioxane-2-carboxylic Acid ¹H NMR: 1.0 (2H, m), 1.4 (4H, m), 1.5 (3H, s), 1.7 (2H, m), 2.0 (1H, m), 2.2 (3H, s), 3.45 (2H, t, J=11.5 Hz), 4.0 (2H, dd, J=11.7 & 4.4 Hz), 4.2 (2H, t, J=6.5 Hz), 6.9 (1H, s), 7.2-7.3 (2H, m), 7.5 (2H, m). Yield: 95%

EXAMPLE 74

5-{4-[1-(2,3-Dimethyl-benzofuran-6-yl)-ethylideneaminooxy]-butyl}-2-methyl-[1,3]dioxane-2-carboxylicacid ¹H NMR: 1.10-1.154 (2H, m), 1.23-1.26 (2H, m), 1.56 (3H, s), 1.66-1.73 (2H, m), 2.04 (1H, m), 2.14 (3H, s), 2.26 (3H, s), 2.38 (3H, s), 3.47 (2H, m), 4.00 (2H, dd, J=11.5028 & 4.068 Hz), 4.17 (2H, t, J=6.13 Hz), 7.35 (1H, d, J=8.1 Hz), 7.51 (1H, d, J=8.01 Hz), 7.62 (1H, s). Yield: 30%

EXAMPLE 75

2-Methyl-5-{4-[1-(1-methyl-1H-indol-3-yl)-ethylideneaminooxy]-butyl}-[1,3]dioxane-2-carboxylic Acid ¹H NMR: 1.08-1.23 (2H, m), 1.39-1.44 (2H, m), 1.55 (3H, s), 1.70-1.77 (2H, m), 2.05 (1H, m), 2.24 (3H, s), 3.46 (2H, t, J=11.52 Hz), 3.79 (3H, s), 3.97 (2H, dd, J=11.95 & 4.032 Hz), 4.19 (2H, t, J=6.39 Hz), 7.17-7.36 (4H, m), 8.27 (1H, d, J=7.8 Hz).
Yield: 90%

EXAMPLE 76

2-Methyl-5-[4-(1-m-tolyl-ethylideneaminooxy)-butyl]-[1,3]dioxane-2-carboxylic Acid ¹H NMR: 1.10 (2H, m), 1.38 (2H, m), 1.57 (3H, s), 1.67 (2H, m), 2.0 (1H, m), 2.21 (3H, s), 2.37 (3H, s), 3.47 (2H, t, J=11.03 Hz), 4.0 (2H, dd, J=4.5 & 12.03 Hz), 4.16 (2H, t. J=6.39 Hz), 7.15-7.27 (2H, m), 7.4 (2H, m). Yield: 75%

EXAMPLE 77

5-{4-[1-(4-Methoxy-phenyl)-propylideneaminooxy]-butyl}-2-methyl-[1,3]dioxane-2-carboxylic Acid ¹H NMR: 1.1 (5H, m), 1.38 (2H, m), 1.56 (3H, s), 1.68 (2H, m), 2.05 (1H, m), 2.71 (2H, q, J=7.57 Hz), 3.46 (2H, t, J=11.58 Hz), 3.82 (3H, s), 4.0 (2H, dd, J=4.5 & 11.92 Hz), 4.12 (2H, t. J=6.33 Hz), 6.89 (2H, d, J=8.8 Hz), 7.55 (21-1, d, J=8.8 Hz).
Yield: 85%

EXAMPLE 78

2-Methyl-5-[4-(1-p-tolyl-propylideneaminooxy)-butyl]-[1,3]dioxane-2-carboxylic Acid ¹H NMR: 1.1 (5H, m), 1.38 (2H, m), 1.57 (3H, s), 1.69 (2H, m), 2.0 (1H, m), 2.35 (3H, s), 2.7 (2H, q. J=7.5 Hz), 3.47 (2H, t, J=11.58 Hz), 3.98 (2H, dd, J=4.44 & 11.88 Hz), 4.13 (2H, t. J=6.33 Hz), 7.15 (2H, d, J=8.0 Hz), 7.52 (2H, d, J=8.1 Hz). Yield: 91%

EXAMPLE 79

2-Methyl-5-[4-(1-pyridin-2-yl-ethylideneaminooxy)-butyl]-[1,3]dioxane-2-carboxylic Acid ¹H NMR: 0.94 (2H, m), 1.26 (3H, s), 1.28 (2H, m), 1.57-1.72 (3H,m), 2.20 (3H, s), 3.53 (2H, t, J=11.14 Hz), 3.63 (2H, dd, J=4.9 & 11.18 Hz), 4.12 (2H, t, J=6.41 Hz), 7.39 (1H, m), 7.8 (2H, m), 8.58 (1H, d, J=4.66 Hz). Yield: 74%

EXAMPLE 80

2-Methyl-5-[4-(1-pyridin-3-yl-ethylideneaminooxy)-butyl]-[1,3]dioxane-2-carboxylic Acid ¹H NMR: 1.10 (2H, m), 1.41 (2H, m), 1.58 (3H, s), 1.67 (2H, m), 2.07 (1H, m), 2.22 (3H, s), 3.58 (2H, t, J=11.58 Hz), 4.0 (2H, dd, J=4.5 & 11.76 Hz), 4.21 (2H, t, J=6.2 Hz), 4.46 (1H, bs), 7.4 (1H, t, J=5.1 Hz), 8.0 (1H, d, J=7.95 Hz), 8.60 (1H, m), 8.95 (1H, s). Yield: 98%

EXAMPLE 81

2-Methyl-5-[4-(1-pyridin-4-yl-ethylideneaminooxy)-butyl]-[1,3]dioxane-2-carboxylic Acid ¹H NMR: 1.10 (2H, m), 1.37 (2H, m), 1.54 (3H, s), 1.7 (2H, m), 2.0 (1H, m), 2.20 (3H, s), 3.53 (2H, t, J=11.64 Hz), 3.97 (2H, dd, J=4.5 & 11.64 Hz), 4.2 (2H, t. J=6.27 Hz), 7.57 (2H, s), 8.62 (2H, s). Yield: 67%

EXAMPLE 82

2-Methyl-5-{4-[1-(5-methyl-furan-2-yl)-ethylidene-aminooxy]-butyl}-[1,3]dioxane-2-carboxylic Acid $^1$H NMR: 0.57-1.13 (2H, m), 1.37 (2H, m), 1.55 (3H, s), 1.67 (2H, m), 2.00 (1H, m), 2.01 (3H, s), 2.34 (3H, s), 3.46 (2H, t, J=9.27 Hz), 3.99 (2H, dd, J=11.61 & 4.5 Hz), 4.15 (2H, m), 6.01 (1H, d, J=2.37 Hz), 6.49 (1H, d, J=3.18 Hz). Yield: 55%.

EXAMPLE 83

Octyl-2-methyl-5-[4-(1-naphthalen-2-yl-ethylidene-aminooxy)-butyl]-[1,3]dioxane-2-carboxylate A mixture of 2-Methyl-5-[4-(1-naphthalen-2-yl-ethylideneaminooxy)-butyl]-[1,3]dioxane-2-carboxylic acid (prepared as per example 63) (0.9 g), n-octyl bromide (0.6 mL) and potassium carbonate (0.64 g) in anhydrous dimethyl formamide (10 mL) was stirred at 60° C. for about 8 hours in an inert atmosphere. The reaction mixture was cooled to ambient temperature, poured into ice cold water and extracted with ethyl acetate. The combined organic extract was washed with water, brine solution, dried over sodium sulphate and evaporated under reduced pressure. Crude product was flash chromatographed over silica gel 8% ethyl acetate in petroleum ether as eluent to obtain 1 g of pure product.

$^1$H NMR: 0.87 (3H, t, J=6.0 Hz), 1.12 (2H, m), 1.27-1.43 (12H, m), 1.50 (3H, s), 1.72 (4H, m), 2.04 (1H, m), 2.33 (3H, s), 3.42 (2H, t, J=11.61 Hz), 3.99 (2H, dd, J=11.88 & 4.5 Hz), 4.23 (4H, t, J=1.71 Hz), 7.46-7.51 (2H, m), 7.78-7.92 (4H, m), 7.98 (1H, s).

Yield: 86%

EXAMPLE 84

Sodium Salt of 2-Methyl-5-[4-(1-naphthalen-2-yl-ethylideneaminooxy)-butyl]-[1,3]dioxane-2-carboxylic Acid To a solution of 2-Methyl-5-[4-(1-naphthalen-2-yl-ethylideneaminooxy)-butyl]-[1,3]dioxane-2-carboxylic acid (prepared as per Example 63) (400 mg) in methanol was added sodium methoxide (56 mg) and stirred at 30° C. for 0.5 hour. Solvent was evaporated under reduced pressure on a rotavapor, residue was triturated with diethyl ether, filtered and dried under vacuum to yield 180 mg of salt.

EXAMPLE 85

L-Arginine Salt of 2-Methyl-5-[4-(1-naphthalen-2-yl-ethylideneaminooxy)-butyl]-[1,3]dioxane-2-carboxylic Acid To a suspension of 2-Methyl-5-[4-(1-naphthalen-2-yl-ethylideneaminooxy)-butyl]-[1,3]dioxane-2-carboxylic acid (prepared in example 63) (1 g) in ethanol was added a solution of L-Arginine (451 mg) in water and the reaction mixture was refluxed for 8 hours. Reaction mixture was cooled to 30° C. and solid separated was filtered and dried under vacuum to obtain 400 mg of the salt.

EXAMPLE 86

Calcium Salt of 5-[4-(1-Benzofuran-2-yl-ethylidene-aminooxy)-butyl]-2-methyl-[1,3]dioxane-2-carboxylic Acid 5-[4-(1-Benzofuran-2-yl-ethylideneaminooxy)-butyl]-2-methyl-[1,3]dioxane-2-carboxylic acid (prepared as per example 72) (3 g) was added to a solution of sodium methoxide (prepared by adding 184 mg of sodium metal to 20 mL of dry methanol) and stirred for 0.5 hour. To this was added a solution of calcium acetate (632 mg) in water. Solid precipitated was filtered and dried under vacuum to yield 3 g of salt. In like manner salts in the table 1 were prepared following the procedure described for the examples 84-86. Following similar process, salts for the other compounds may also be prepared.

TABLE 1

| Example No. | Free-acid example No. | Salt prepared | Melting Point (° C.)* |
|---|---|---|---|
| 84 | 63 | Na | 240 |
| 85 | 63 | L-Arginine | 230 (decomposed) |
| 86 | 72 | Ca | 250 (decomposed) |
| 87 | 72 | L-Arginine | 212 |
| 88 | 53 | Ca | 250 |
| 89 | 53 | L-Arginine | 200 |
| 90 | 75 | L-Arginine | 224 |

*The melting points were uncorrected and may vary in the range of ±4° C.

The compounds of the present invention lowered triglyceride, total cholesterol, LDL, VLDL and increased HDL and lowered serum glucose levels. This was demonstrated by in vitro as well as in vivo animal experiments.

A) Demonstration of In Vitro Efficacy of Compounds:

In vitro hPPAR α & hPPARγ activities were determined as per in-house protocols and the results of representative compounds are provided in table 2 below as a proof of the efficacies of the novel class of compounds disclosed above.

TABLE 2

| Example No. | EC$_{50}$(PPAR alpha) □M | EC$_{50}$(PPAR gamma)□M |
|---|---|---|
| 44 | 0.08 | 5.1 |
| 46 | 0.14 | 7.2 |
| 48 | 0.17 | 15 |
| 49 | 0.3 | 11.9 |
| 52 | 0.03 | 4 |
| 55 | 0.06 | 5.2 |
| 56 | 0.08 | 2.9 |
| 57 | 0.04 | 11.4 |
| 59 | 0.13 | 41.4 |
| 60 | 0.01 | 0.8 |
| 61 | 0.05 | 38.8 |
| 62 | 0.02 | 0.9 |
| 84 | 0.004 | 1.9 |
| 64 | 0.004 | 2 |
| 66 | 0.19 | 8 |
| 67 | 1.2 | 35 |
| 68 | 2.7 | 16.5 |
| 69 | 0.15 | 5.5 |
| 70 | — | 0.2 |
| 76 | 0.1 | 11 |
| 77 | 0.28 | 3.5 |
| 78 | 0.08 | 3.9 |

B) Demonstration of In Vivo Efficacy of Compounds:

i) Serum Triglyceride Lowering Activity in Swiss Albino Mice:

Male Swiss albino mice (SAM) were bred in Zydus animal house. All these animals were maintained under 12 hour light and dark cycle at 25±1° C. Animals were given standard laboratory chow (NIN, Hyderabad, India) and water ad libitum. SAM of 20-30 g body weight range was used. The protocol approved by Institutional Animal Ethics Committee is being used.

The test compounds were administered orally to Swiss albino mice at 0.001 to 50 mg/kg/day dose for 6 days. The compound was administered after suspending it in 0.25% CMC or dissolving it in water, when compound is water-soluble. Control mice were treated with vehicle (0.25% of Carboxymethyl cellulose; dose 10 ml/kg).

The blood samples were collected on $0^{th}$ day and in fed state 1 hour after drug administration on $6^{th}$ day of the treatment. The blood was collected in non heparinised capillary and the serum was analyzed for triglyceride (Wieland, O. Methods of Enzymatic analysis. Bergermeyer, H., O., Ed., 1963. 211-214; Trinder, P. Ann. Clin. Biochem. 1969. 6: 24-27). Measurement of serum triglyceride was done using commercial kits (Zydus-Cadila, Pathline, Ahmedabad, India).

Formula for Calculation:
Percentage Reduction in Triglycerides was Calculated According to the Formula:

$$\text{Percentage reduction (\%)} = 1 - \left[\frac{TT/OT}{TC/OC}\right] \times 100$$

$OC$ = Zero day control group value $OT$ = Zero day treated group value $TC$ = Test day control group $TT$ = Test day treated group

TABLE 3

Triglyceride lowering activity in Swiss albino mice:

| Example No. | Dose (mg/kg/day) | % Triglyceride lowering |
|---|---|---|
| 44 | 10 | 40 |
| 46 | 10 | 39 |
| 48 | 10 | 64 |
| 49 | 10 | 51 |
| 52 | 10 | 36 |
| 55 | 10 | 46 |
| 57 | 10 | 43 |
| 59 | 10 | 22 |
| 60 | 10 | 62 |
| 61 | 10 | 44 |
| 62 | 10 | 69 |
| 63 | 10 | 84 |
| 64 | 10 | 85 |
| 66 | 10 | 50 |
| 67 | 10 | 75 |
| 68 | 10 | 33 |
| 69 | 10 | 61 |
| 70 | 10 | 49 |
| 76 | 10 | 67 |
| 77 | 10 | 39 |
| 78 | 10 | 42 |
| 83 | 10 | 61 | iI) Serum Glucose Lowering Activity in db/db Mice Models

Homozygous animal $C_{57}BL/KsJ$-db/db mice are obese, hyperglycemic, hyperinsulinemic and insulin resistant (J. Clin. Invest, 85, 962-967, 1990), whereas heterozygous are lean and normoglycemic. The homozygous animals very closely mimic the human type II diabetes when blood sugar levels are not sufficiently controlled. Since this type of model resembles human type II diabetes mellitus, the compounds of the invention were tested for their antidiabetic activity in this model.

The compounds of the present invention showed serum glucose and triglycerides lowering activities.

Male $C_{57}BL/KsJ$-db/db mice of 8 to 14 weeks age, having body weight range of 40 to 60 grams, procured from the Jackson Laboratory, USA, were used in the experiment.

Test compounds were suspended on 0.25% carboxymethyl cellulose or dissolved in water when the compound is water soluble and administered to test group containing 6 animals at a dose of 0.001 mg to 50 mg/kg through oral gavage daily for 6 days. The control group received vehicle (dose 10 ml/kg). On the $6^{th}$ day, one hour after the drug dosing, blood was collected from retro-orbital sinus and the serum was analyzed for glucose and triglycerides were measured using commercial kits (Zydus-Cadila, Pathline, Ahmedabad, India). The serum glucose and triglyceride lowering activities of the test compound was calculated according of the formula:

$$\text{Serum glucose/triglycerides lowering activity (\%)} = 1 - \left[\frac{TT/OT}{TC/OC}\right] \times 100$$

$OC$ = Zero day control group value $OT$ = Zero day treated group value $TC$ = Test day control group $TT$ = Test day treated group

TABLE 4

Serum glucose & triglycerides lowering activity in db/db mice:

| Example No. | Dose (mg/kg/day) | Serum Glucose reduction (%) | Plasma TG reduction (%) |
|---|---|---|---|
| 48 | 3 | 14 | 44 |
| 63 | 3 | 41 | 59 |
| 64 | 3 | 31 | 46 |
| 66 | 3 | 27 | 45 |
| 67 | 3 | 12 | 48 |
| 70 | 3 | 26 | 52 |

No adverse effects were observed for any of the mentioned compounds of invention. The compounds of the present invention showed good serum glucose, lipid and cholesterol lowering activity in the experimental animals used. These compounds are useful for the testing/prophylaxis of diseases caused by hyperlipidemia, hypercholesterolemia, hyperinsulinemia, hyperglycemia such as NIDDM, cardiovascular diseases, stroke, hypertension, obesity since such diseases are interlinked to each other.

We claim:

1. A 1,3-dioxane carboxylic acid of formula (I), $$\underset{B}{\overset{A}{>}}=N-O-(CH_2)_m-\underset{O}{\overset{O}{\diagdown}}\underset{C(O)OR_2}{\overset{R_1}{\diagup}}$$ (I)

a tautomeric form, a stereoisomer, or a pharmaceutically acceptable salt thereof, wherein A represents an optionally substituted single or fused group selected from aryl, heteroaryl, and heterocyclyl groups; B represents substituted or unsubstituted linear or branched ($C_1$—$C_6$)alkyl group; m represents an integer from 2-6; $R_1$ represents ($C_1$—$C_3$)alkyl group and $R_2$ represents hydrogen, or a ($C_1$—$C_3$) alkyl group.

2. The compound as claimed in claim 1, wherein the aryl group is selected from monocyclic, bicyclic and tricyclic aryl groups.

3. The compound as claimed in claim 1, wherein the aryl group is selected from phenyl, naphthyl, tetrahydronaphthyl, indane and biphenyl groups.

4. The compound as claimed in claim 1, wherein the heterocyclyl is selected from saturated, partially saturated or unsaturated aromatic or non-aromatic mono, bi or tricyclic groups, containing one or more heteroatoms selected from N, O, and S.

5. The compound as claimed in claim 1, wherein the heterocyclcyl group is selected from pyrrolidinyl, imidazolidinyl, piperidinyl, piperazinyl, morpholinyl, oxazolidinyl, and thiazolidinyl.

6. The compound according to claim 4, wherein the partially saturated heterocyclic radical is selected from dihydrothiophene, dihydropyran, dihydrofuran, and dihydrothiazole groups.

7. The compound as claimed in claim 1, wherein the heteroaryl group is selected from 5 to 8 membered aromatic radicals, which may be single or fused containing one or more hetero atoms selected from O, N or S.

8. The compound as claimed in claim 1, wherein the heteroaryl group is selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzothiazolyl, benzimidazolyl, benzotriazolyl, phthalazynil, naphthylidinyl, purinyl, carbazolyl, phenothiazinyl, and phenoxazinyl groups.

9. The compound as claimed in claim 1, wherein when A is substituted, the substituents are selected from hydroxyl, oxo, halo, thio, or optionally substituted groups selected from alkyl, haloalkyl, alkoxy, alkoxyalkyl, haloalkoxy, cycloalkyl, alkoxy, cycloalkoxy, aryl, aryloxy, aralkyl, aralkoxy, heteroaryl, heteroaralkyl, heteroaryloxy, acyl, acyloxy, hydroxyalkyl, alkoxyalkyl, aryloxyalkyl, aralkoxyalkyl, alkylthio, thioalkyl, arylthio, alkylsulfonyloxy, sulfenyl derivatives and sulfonyl derivatives.

10. The compound as claimed in claim 9, wherein when the substituents on A are further substituted, those substituents are selected from hydroxyl, oxo, halo, thio, or substituted or unsubstituted groups selected from alkyl, haloalkyl, alkoxy, haloalkoxy, acyl, acyloxy, alkylthio, thioalkyl, alkylsulfonyloxy, alkoxycarbonylamino, sulfenyl derivatives and sulfonyl derivatives.

11. A compound as claimed in claim 1, selected from:
Methyl-2-methyl-5-[4-(1-phenyl-ethylideneaminooxy)-butyl]-[1,3]dioxane-2-carboxylate;
Methyl-2-methyl-5-[4-(1-phenyl-pentylideneaminooxy)-butyl]-[1,3]dioxane-2-carboxylate;
Methyl-5-(4-benzylideneaminooxy-butyl)-2-methy-[1,3]dioxane-2-carboxylate;
Methyl-2-methyl-5-{4-[1-(4-trifluoromethyl-phenyl)-ethylideneaminooxy]-butyl}-[1,3]dioxane-2-carboxylate;
Methyl-5-{4-[1-(4-fluoro-phenyl)-ethylideneaminooxy]-butyl}-2-methyl-[1,3]dioxane-2-carboxylate;
Methyl-5-{4-[1-(4-chloro-phenyl)-ethylideneaminooxy]-butyl}-2-methyl-[1,3]dioxane-2-carboxylate;
Methyl-5-{4-[1(4-methanesulfonyl-phenyl)-ethylideneaminooxy]-butyl}-2-methyl-[1,3]dioxane-2-carboxylate;
Methyl-(2-methyl-5-[4-(1-m-tolyl-ethylideneaminooxy)-butyl]-[1,3]dioxane-)-2-carboxylate;
Methyl-5-{4-[1-(4-butyl-phenyl)-ethylideneaminooxy]-butyl}-2-methyl-[1,3]dioxane-2-carboxylate;
Methyl-2-methyl-5[4-(1-p-tolyl-ethylideneaminooxy)-butyl]-[1,3]dioxane-2-carboxylate;
Methyl-2-methyl-5-{4-[1-(4-methylsulfanyl-phenyl)-ethylideneaminooxy]-butyl}-[1,3]dioxane-2-carboxylate;
Methyl-5-{4-[1-(4-ethyl-phenyl)-ethylideneaminooxy]-butyl}-2-methyl-[1,3]dioxane-2-carboxylate;
Methyl-5-{4-[1-(4-ethoxy-phenyl)-ethylideneaminooxy]-butyl}-2-methyl-[1,3]dioxane-2-carboxylate;
Methyl-5-{4-[1-(4-isopropoxy-phenyl)-ethylideneaminooxy]-butyl}-2-methyl-[1,3]dioxane-2-carboxylate;
Methyl-2-methyl-5-{4-[1-(4-phenoxy-phenyl)-ethylideneaminooxy]-butyl}-[1,3]dioxane-2-carboxylate;
Methyl-5-{4-[1-(4-isobutyl-phenyl)-ethylideneaminooxy]-butyl}-2-methyl-[1,3]dioxane-2-carboxylate;
Methyl-5-{4-[1-(4-methoxy-phenyl)-ethylideneaminooxy]-butyl}-2-methyl-[1,3]dioxane-2-carboxylate;
Methyl-5-[4-(1-biphenyl-4-yl-ethylideneaminooxy)-butyl]-2-methyl-[1,3]dioxane-2-carboxylate;
Methyl-5-{4-[1-(3-chloro-4-fluoro-phenyl)-ethylideneaminooxy]-butyl}-2-methyl-[1,3]dioxane-2-carboxylate;
Methyl-5-{4-[1-(3,4-dimethyl-phenyl)-ethylideneaminooxy]-butyl}-2-methyl-[1,3]dioxane-2-carboxylate;
Methyl-5-{5-[1-(3,4-dimethyl-phenyl)-ethylideneaminooxy]-pentyl}-2-methyl-[1,3]dioxane-2-carboxylate;
Methyl-5-{4-[1(4-methoxy-3-methyl-phenyl)-ethylideneaminooxy]-butyl}-2-methyl-[1,3]dioxane-2-carboxylate;
Methyl-5-{4-[1(3,4-dimethoxy-phenyl)-ethylideneaminooxy]-butyl}-2-methyl-[1,3]dioxane-2-carboxylate;
Methyl-5-{4-[1(3-Fluoro-4-methoxy-phenyl)-ethylideneaminooxy]-butyl}-2-methyl-[1,3]dioxane-2-carboxylate;
Methyl-(5-{4-[1(4-methoxy-phenyl)-propylideneaminooxy]-butyl}-2-methyl-[1,3]dioxane-)-2-carboxylate;
Methyl-{2-methyl-5-[4-(1-p-tolyl-propylicleneaminooxy)-butyl]-[1,3]dioxane}-2-carboxylate;
Methyl-{2-methyl-5-[4-(1-pyridin-2-yl-ethylideneatninooxy)-butyl]-[1,3]dioxane}-2-carboxylate;
Methyl-{2-methyl-5-[4-(1-pyridin-3-yl-ethylicleneaminooxy)-butyl]-[1,3]dioxane}-2-carboxylate;
Methyl-{2-methyl-5-[4-(1-pyridin-4-yl-ethylideneaminooxy)-butyl]-[1,3]dioxane}-2-carboxylate;
Methyl-5-[4-(1-benzo[1,3]dioxol -5-yl-ethylicleneaminooxy)-butyl]-2-methyl-[1,3]dioxane-2-carboxylate;
Methyl-2-methyl-5-[4-(1-thiophen-2-yl-ethylicleneaminooxy)-butyl]-[1,3]dioxane-2-carboxylate;
Methyl-5-[4-(1-benzofuran-2-yl-ethylideneaminooxy)-butyl]-2-methyl-[1,3]dioxane-2-carboxylate;
Methyl-5-[5-(1-benzofuran-2-yl-ethylicieneaminooxy)-pentyl]-2-methyl-[1,3]dioxane-2-carboxylate;
Methy-5-{4-[1-(2,3-dimethyl-benzofuran-6-yl)-ethylideneaminooxy]-butyl}-2-methyl-[1,3]dioxane-2-carboxylate;

Methyl-2-methyl-5-{4-[1(1-methyl-1H-indol-3-yl)-ethylideneaminooxy]-butyl}-[1,3]dioxane-2-carboxylate;
Methyl-2-methyl-5-[5-(1-naphthalen-2-yl-ethyliclene-aminooxy)-pentyl]-[1,3]dioxane-2-carboxylate;
Methyl-2-methyl-5-[4-(1-naphthalen-2-yl-ethyliclene-aminooxy)-butyl]-[1,3]dioxane-2-carboxylate;
Methyl-2-methyl-5-{4-[1-(5,6,7,8-tetrahyciro-naphthalen-2-yl)-ethylideneaminooxy]-butyl}-[1,3]dioxane-2-carboxylate;
Methyl-5-{4-[1-(4-methoxymethoxy-phenyl)-ethylideneaminooxy]-butyl}-2-methyl-[1,3]dioxane-2-carboxylate;
Methyl-5-{4-[1-(4-hydroxy-phenyl)-ethylideneamínooxy]-butyl}-2-methyl-[1,3]dioxane-2-carboxylate;
Methyl-5-{4-[1-(4-methanesulfonyloxy-phenyl)-ethylideneaminooxy]-butyl}-2-methyl-[1,3]dioxane-2-carboxylate;
Octyl-2-methyl-5-[4-(1-naphthalen-2-yl-ethylideneaminooxy)-butyl]-[1,3]dioxane-2-carboxylate;
2-Methyl-5-[4-(1-phenyl-ethylideneaminooxy)-butyl]-[1,3]dioxane-2-carboxylic acid and its pharmaceutically acceptable salts;
5-(4-Benzylideneaminooxy-butyl)-2-methyl-[1,3]dioxane-2-carboxylic acid and its pharmaceutically acceptable salts;
2-Methyl-5-{4-[1-(4-trifluoromethyl-phenyl)-ethylideneaminooxy]-butyl}-[1,3]dioxane-2-carboxylic acid and its pharmaceutically acceptable salts;
5-{4-[1-(4-Fluoro-phenyl)-ethylideneaminooxy]-butyl}-2-methyl-[1,3]dioxane-2-carboxylic acid and its pharmaceutically acceptable salts;
5-{4-[1-(4-Chloro-phenyl)-ethylideneaminooxy]-butyl}-2-methyl-[1,3]dioxane-2-carboxylic acid and its pharmaceutically acceptable salts;
5-{4-[1-(4-Methanesulfonyl-phenyl)-ethylideneaminooxy]-butyl}-2-methyl-[1,3]dioxane-2-carboxylic acid and its pharmaceutically acceptable salts;
2-Methyl-5-[4-(1-p-tolyl-ethylideneaminooxy)-butyl]-[1,3]dioxane-2-carboxylic acid and its pharmaceutically acceptable salts;
5-{4-[1-(3-Chloro-4-fluoro-phenyl)-ethylideneaminooxy]-butyl}-2-methyl-[1,3]dioxane-2-carboxylic acid and its pharmaceutically acceptable salts;
5-{4-[1-(4-Butyl-phenyl)-ethylideneaminooxy]-butyl}-2-methyl-[1,3]dioxane-2-carboxylic acid and its pharmaceutically acceptable salts;
2-Methyl-5-{4-[1-(4-methylsulfanyl-phenyl)-ethylideneaminooxy]-butyl}-[1,3]dioxane-2-carboxylic acid and its pharmaceutically acceptable salts;
5-{4-[1-(4-Ethyl-phenyl)-ethylideneaminooxy]-butyl}-2-methyl-[1,3]dioxane-2-carboxylic acid and its pharmaceutically acceptable salts;
5-{4-[1-(3,4-Dimethyl-phenyl)-ethylideneaminooxy]-butyl}-2-methyl-[1,3]dioxane-2-carboxylic acid and its pharmaceutically acceptable salts;
5-{5-[1-(3,4-Dimethyl-phenyl)-ethylideneaminooxy]-pentyl}-2-methyl-[1,3]dioxane-2-carboxylic acid and its pharmaceutically acceptable salts;
5-{4-[1-(4-Ethoxy-phenyl)-ethylideneaminooxy]-butyl}-2-methyl-[1,3]dioxane-2-carboxylic acid and its pharmaceutically acceptable salts;
5-{4-[1-(4-Isopropoxy-phenyl)-ethylideneaminooxy]-butyl}-2-methyl-[1,3]dioxane-2-carboxylic acid and its pharmaceutically acceptable salts;
5-{4-[1-(4-Methoxy-3-methyl-phenyl)-ethylideneaminooxy]-butyl}-2-methyl-[1,3]dioxane-2-carboxylic acid and its pharmaceutically acceptable salts;
2-Methyl-5-{4-[1-(4-phenoxy-phenyl)-ethylideneaminooxy]-butyl}-[1,3]dioxane-2-carboxylic acid and its pharmaceutically acceptable salts;
5-{4-[1-(3,4-Dimethoxy-phenyl)-ethylideneaminooxy]-butyl}-2-methyl-[1,3]dioxane-2-carboxylic acid and its pharmaceutically acceptable salts;
5-{4-[1-(4-Isobutyl-phenyl)-ethylideneaminooxy]-butyl}-2-methyl-[1,3]dioxane-2-carboxylic acid
5-{4-[1-(3-Fluoro-4-methoxy-phenyl)-ethylideneaminooxy]-butyl}-2-methyl-[1,3]dioxane-2-carboxylic acid and its pharmaceutically acceptable salts;
2-Methyl-5-[5-(1-naphthalen-2-yl-ethylideneaminooxy)-pentyl]-[1,3]dioxane-2-carboxylic acid and its pharmaceutically acceptable salts;
2-Methyl-5-[4-(1-naphthalen-2-yl-ethylideneaminooxy)-butyl]-[1,3]dioxane-2-carboxylic acid and its pharmaceutically acceptable salts;
2-Methyl-5-{4-[1-(5,6,7,8-tetrahydro-naphthalen-2-yl)-ethylideneaminooxy]-butyl}-[1,3]dioxane-2-carboxylic acid and its pharmaceutically acceptable salts;
5-{4-[1-(4-Hydroxy-phenyl)-ethylideneaminooxy]-butyl}-2-methyl-[1,3]dioxane-2-carboxylic acid and its pharmaceutically acceptable salts;
5-{4-[1-(4-Methoxy-phenyl)-ethylideneaminooxy]-butyl}-2-methyl-[1,3]dioxane-2-carboxylic acid and its pharmaceutically acceptable salts;
5-{4-[1-(4-Methanesulfonyloxy-phenyl)-ethylideneaminooxy]-butyl}-2-methyl-[1,3]dioxane-2-carboxylic acid and its pharmaceutically acceptable salts;
2-Methyl-5-[4-(1-thiophen-2-yl-ethylideneaminooxy)-butyl]-[1,3]dioxane-2-carboxylic acid and its pharmaceutically acceptable salts;
5-[4-(1-Benzo[1,3]dioxol-5-yl-ethylideneaminooxy)-butyl]-2-methyl-[1,3]dioxane-2-carboxylic acid and its pharmaceutically acceptable salts;
5-[4-(1-Biphenyl-4-yl-ethylideneaminooxy)-butyl]-2-methyl-[1,3]dioxane-2-carboxylic acid and its pharmaceutically acceptable salts;
2-Methyl-5[4(1-phenyl-pentylideneaminooxy)-butyl]-[1,3]dioxane-2-carboxylic acid and its pharmaceutically acceptable salts;
5-[4-(1-Benzofuran-2-yl-ethylideneaminooxy)-butyl]-2-methyl-[1,3]dioxane-2-carboxylic acid and its pharmaceutically acceptable salts;
5-[5-(1-Benzofuran-2-yl-ethylideneaminooxy)-pentyl]-2-methyl-[1,3]dioxane-2-carboxylic acid and its pharmaceutically acceptable salts;
5-{4-[1-(2,3-Dimethyl-benzofuran-6-yl)-ethylideneaminooxy]-butyl}-2-methyl-[1,3]dioxane-2-carboxylic acid and its pharmaceutically acceptable salts;
2-Methyl-5-{4[1-(1-methyl-1H-indol-3-yl)-ethylideneaminooxy]-butyl}-[1,3]dioxane-2-carboxylic acid and its pharmaceutically acceptable salts;
2-Methyl-5-[4-(1-m-tolyl-ethylideneaminooxy)-butyl]-[1,3]dioxane-2-carboxylic acid and its pharmaceutically acceptable salts;
5-{4-[1-(4-Methoxy-phenyl)-propylideneaminooxy]-butyl}-2-methyl-[1,3]dioxane-2-carboxylic acid and its pharmaceutically acceptable salts;
2-Methyl-5-[4-(1-p-tolyl-propylideneaminooxy)-butyl]-[1,3]dioxane-2-carboxylic acid and its pharmaceutically acceptable salts;
2-Methyl-5-[4-(1-pyridin-2-yl-ethylideneaminooxy)-butyl]-[1,3]dioxane-2-carboxylic acid and its pharmaceutically acceptable salts;

2-Methyl-5-[4-(1-pyridin-3-yl-ethylideneaminooxy)-butyl]-[1,3]dioxane-2-carboxylic acid and its pharmaceutically acceptable salts;

2-Methyl-5-[4-(1-pyridin-4-yl-ethylideneaminooxy)-butyl]-[1,3]dioxane-2-carboxylic acid and its pharmaceutically acceptable salts; and 2-Methyl-5-{4-[1-(5-methyl-furan-2-yl)-ethylideneaminooxy]-butyl}-[1,3]dioxane-2-carboxylic acid and its pharmaceutically acceptable salts.

12. A pharmaceutical composition which comprises a compound of formula (I) as defined in claim 1, or a pharmaceutically acceptable salt thereof and one or more of pharmaceutically acceptable carriers, diluents or excipients.

13. A pharmaceutical composition which comprises a compound as defined in claim 11, or a pharmaceutically acceptable salt thereof and one or more of pharmaceutically acceptable carriers, diluents or excipients.

14. A method of preventing or treating a disease selected from or caused by hyperlipidemia, hypercholesteremia, hyperglycemia, obesity, impaired glucose tolerance, leptin resistance, insulin resistance, diabetic complications, comprising administering an effective, non-toxic amount of compound of formula (I) or its pharmaceutically acceptable salt thereof as defined in claim 1 to a patient in need thereof.

15. A method of preventing or treating a disease selected from or caused by hyperlipidemia, hypercholesteremia, hyperglycemia, obesity, impaired glucose tolerance, leptin resistance, insulin resistance, diabetic complications, comprising administering an effective, non-toxic amount of compound of formula (I) or its pharmaceutically acceptable salt thereof as defined in claim 11 to a patient in need thereof.

16. A method of preventing or treating a disease selected from or caused by hyperlipidemia, hypercholesteremia, hyperglycemia, obesity, impaired glucose tolerance, leptin resistance, insulin resistance, diabetic complications, comprising administering an effective, non-toxic amount of the composition according to claim 12 to a patient in need thereof.

17. A method of preventing or treating a disease selected from or caused by hyperlipidemia, hypercholesteremia, hyperglycemia, obesity, impaired glucose tolerance, leptin resistance, insulin resistance, diabetic complications, comprising administering an effective, non-toxic amount of the composition according to claim 13 to a patient in need thereof.

18. A method according to claim 14, wherein the disease is type 2 diabetes, impaired glucose tolerance, dyslipidaemia, hypertension, obesity, atherosclerosis, hyperlipidaemia, coronary artery disease, cardiovascular disorders and other diseases wherein insulin resistance is the underlying pathophysiologal mechanism.

19. A method according to claim 16, wherein the disease is type 2 diabetes, impaired glucose tolerance, dyslipidaemia, hypertension, obesity, atherosclerosis, hyperlipidaemia, coronary artery disease, cardiovascular disorders and other diseases wherein insulin resistance is the underlying pathophysiologal mechanism.

20. A process for preparing a compound of formula (I) as claimed in claim 1 comprising:
a) reacting a compound of general formula (II) where all symbols are as defined in claim 1 with a compound of general formula (III), where all symbols are as defined in claim 1 and L represents a suitable leaving group selected from halogen, mesylate, tosylate, and triflate and $R_2$ represent alkyl to yield compound of formula (I) where all symbols are as defined in claim 1 and $R_2$ represent $(C_1-C_3)$alkyl group

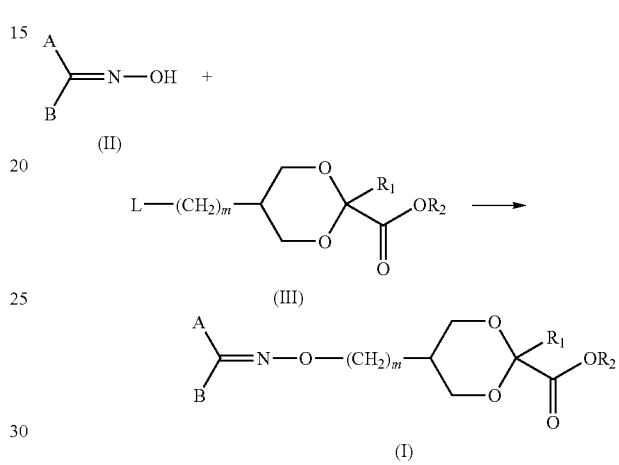

and
b) hydrolysing the compound of general formula (I) wherein $R_2$ is alkyl group as defined earlier, and all other symbols are as defined earlier to yield a compound of formula (I) wherein $R_2$ is H and all other symbols are as defined in claim 1.

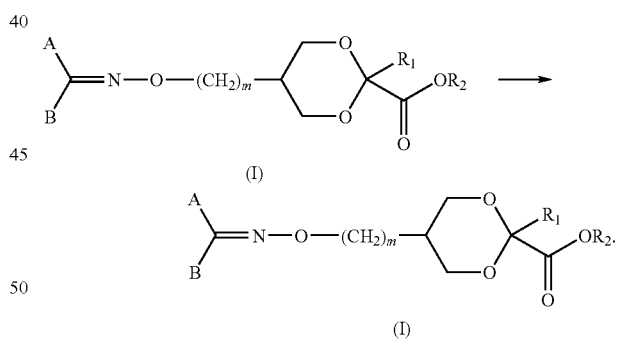

* * * * *